United States Patent [19]

Treves

[11] 4,092,150

[45] May 30, 1978

[54] HERBICIDAL 5-PYRIMIDINECARBONITRILES

[75] Inventor: Gino R. Treves, Princeton, N.J.

[73] Assignee: FMC Corporation, Philadelphia, Pa.

[21] Appl. No.: 811,917

[22] Filed: Jun. 30, 1977

Related U.S. Application Data

[63] Continuation-in-part of Ser. No. 718,224, Aug. 27, 1976, abandoned.

[51] Int. Cl.² .................. A01N 9/22; C07D 239/34
[52] U.S. Cl. .................................. 71/92; 544/320; 544/321; 544/323; 544/326; 544/330; 544/319; 544/334; 544/301
[58] Field of Search ............... 260/256.4 N, 256.4 C; 71/92

[56] References Cited

U.S. PATENT DOCUMENTS

| | | | |
|---|---|---|---|
| 3,097,910 | 7/1963 | Andrew et al. | 260/256.4 N |
| 3,178,432 | 4/1965 | Druey et al. | 260/256.4 C |
| 3,226,424 | 12/1965 | Jampolsky et al. | 260/256.4 N |
| 3,830,812 | 8/1974 | Ramsey | 260/256.4 N |
| 3,845,055 | 10/1974 | Hoegerle et al. | 260/256.4 N |
| 3,910,913 | 10/1975 | Kim, et al. | 260/256.4 N |

OTHER PUBLICATIONS

Friefelder, et al. "J. Amer. Chem. Soc.", vol. 82, 1960, p. 696.
Goldner, et al., "J. Prakt. Chem.", vol. 12, 1961, p. 242.
Martin, et al., "Pesticide Manual," 4th ed. (England) 1974, p. 23.
Huber, "J. Amer. Chem. Soc.", vol. 65, 1943, p. 2222.
Martin, et al., "Pesticide Manual," 4th Ed. (England) 1974, pp. 137, 146, 449 and 477.
Scarborough, et al., "J. Org. Chem.", vol. 26, 1961, p. 3720.

*Primary Examiner*—Donald G. Daus
*Assistant Examiner*—James H. Turnipseed
*Attorney, Agent, or Firm*—Richard L. Hansen; Henry R. Ertelt

[57] ABSTRACT

5-Pyrimidinecarbonitriles, having amino substituents in the 2 and 6 positions and an alkoxy substituent in the 4 position, exhibit herbicidal activity. The preparation of novel active compounds and intermediates in this class is described; herbicidal compositions containing the active compounds are illustrated; and methods for utilizing the herbicidal compositions to control plant growth are disclosed.

22 Claims, No Drawings

HERBICIDAL 5-PYRIMIDINECARBONITRILES

REFERENCE TO PRIOR APPLICATION

This is a Continuation-In-Part of Application Ser. No. 718,224, filed Aug. 27, 1976, now abandoned.

BACKGROUND OF THE INVENTION

1. Field of the Invention

This is a continuation-in-part of application Ser. cides, to novel herbicidal compounds and intermediates thereto, as well as to compositions containing the active compounds, and to new methods for the control of undesired plant growth by preemergence or postemergence application of the novel active compounds and compositions.

2. Description of the Prior Art

It has long been man's desire to promote the growth of certain plant species, those species which serve as food for man or for his animals, species which protect him from the elements, such as trees and shrubbery, and species which he finds aesthetically attractive, such as flowers. Centuries ago man learned to promote the growth of plants by applying fertilizer to them. Great commercial enterprises have been built upon processes for producing ammonia, urea, phosphates, potash, and other materials incorporated into fertilizer compositions. The value in the use of fertilizer for promoting plant growth is well known.

Man has probably always realized that certain foreign plant species, weeds, compete with his crops for the available sunlight, air, and nutrients in the soil. However, it is only recently, with the exponential growth in the world's population and the resultant demands placed upon the world's food supply, that man has developed the technical ability to selectively retard or prevent the growth of undesired plant species growing with his crops. One of the first herbicides was 2,4-dichlorophenoxyacetic acid (2,4-D), which became available in 1944 for the control of broad-leaved weeds. Since then, a number of other classes of herbicides have appeared, some of which are more selective than 2, 4-D, give control at much lower rates of application, are less toxic to mammals, longer lasting, easier to use, cheaper, and do not leave residues harmful to the environment. All of these characteristics are desirable features for a herbicide to possess.

Heterocyclic organic compounds are among the newer classes of herbicides. For example, the six-member s-triazine ring system is the central structural feature in a number of commercial herbicides, including 2-t-butylamino-4-ethylamino-6-methoxy-s-triazine [Martin and Worthing, "Pesticide Manual," 4th Ed., British Crop Protection Council, Worcester, England, 1974, p. 477], 2-sec-butylamino-4-ethylamino-6-methoxy-s-triazine [ibid., p. 449], 2-chloro-4-cyclopropylamino-6-isopropylamino-s-triazine [ibid., p. 146], 2-chloro-4-ethylamino-6-isopropylamino-s-triazine [ibid., p. 23], and 2-chloro-4-(1-cyano-1-methylethylamino)-6-ethylamino-s-triazine [ibid., p. 137].

The six member 1,3-diazine (pyrimidine) ring system is less common among the known herbicides, but some 4,6-disubstituted and 2,4,6-trisubstituted 5-nitropyrimidines display herbicidal activity [Ger. Offen. 2,520,381]as do certain 2,6-diamino-5-pyrimidinecarboxamides [U.S. Pat. No. 3,845,055].

It has now been discovered that 5-pyrimidinecarbonitriles, having amino substituents in the 2 and 6 positions and an alkoxy substituent in the 4 position, are extremely effective herbicides, which control the growth of a range of grassy and broad-leaved weeds while not affecting desirable crops such as corn and cotton growing therewith. One advantage of the 2,4,6-trisubstituted 5-pyrimidinecarbonitriles of this invention is that many of them are effective at very low rates of application.

SUMMARY OF THE INVENTION

The novel active 5-pyrimidinecarbonitriles of this invention and the novel compounds useful as intermediates thereto are represented collectively by the following structural formula:

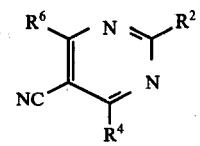

wherein $R^2$ is a radical selected from amino, lower alkylamino, lower cycloalkylamino, di(lower alkyl)amino, [alpha-cyano(lower alkyl)]amino, and halogen; $R^4$ is a radical selected from lower alkoxy, and halogen; and $R^6$ is a radical selected from amino, lower alkylamino, lower cycloalkylamino, di(lower alkyl)amino, and halogen; with the proviso that no more than two of $R^2$, $R^4$ and $R^6$ are halogen; and provided further that neither $R^2$ nor $R^6$ is tert-butylamino; and when $R^2$ is isopropylamino, $R^6$ is other than n-butylamino; and when $R^2$ is methylethylamino, $R^6$ is other than isopropylamino; and when $R^2$ is diethylamino, $R^6$ is other than amino. In defining $R^2$, $R^4$, and $R^6$, the term "lower" means 1-7 carbon atoms, preferably 1-4 carbon atoms.

These novel intermediates and the novel active 5-pyrimidinecarbonitriles prepared therefrom can be obtained conveniently from a 2,4,6-trihalo-5-pyrimidinecarbonitrile. 2,4,6-Trichloro-5-pyrimidinecarbonitrile is available from barbituric acid and urea via 2,4,6-trihydroxy-5-pyrimidinecarboxamide [Scarborough and Gould, J. Org. Chem., 26, 3720 (1961); U.S. Pat. No. 3,097,910]. Alpha-aminonitriles are employed in preparing 5-pyrimidinecarbonitriles containing an [alphacyano(lower-alkyl)]amino group in the $R^2$ position. Alpha-aminonitriles may be prepared by the Strecker synthesis [Freifelder and Hasbrouck, J. Amer. Chem. Soc., 82, 696 (1960)].

The novel intermediates of this invention contain at least one, but no more than two, halogen atoms, preferably chlorine. They are obtained by the displacement of one or two of the halogen atoms of a 2,4,6-trihalo-5-pyrimidinecarbonitrile. Among the former, especially useful intermediates comprise 4,6-dichloro-2-(1-cyano-1-methylethylamino)-5-pyrimidinecarbonitrile, 4,6-dichloro-2-isopropylamino-5-pyrimidinecarbonitrile and 4,6-dichloro-2-(1-methylpropylamino)-5-pyrimidinecarbonitrile; whereas among the latter, 4-chloro-2-(1-cyano-1-methylethylamino)-6-ethylamino-5-pyrimidinecarbonitrile, 4-chloro-2-(1-cyano-1-methylethylamino)-6-isopropylamino-5-pyrimidinecarbonitrile, 4-chloro-2-(1-cyano-1-methylethylamino)-6-cyclopropylamino-5-pyrimidinecarbonitrile, 4-chloro-6-cyclopropylamino-2-isopropylamino-5-pyrimidinecarbonitrile, and 4-chloro-6-cyclopropylamino-2-(1-methylpropylamino)-5-pyrimidinecarbonitrile are especially useful.

In the novel active 5-pyrimidinecarbonitriles of this invention all three of the halogen atoms of the 2,4,6-trihalo-5-pyrimidinecarbonitrile are displaced, so that $R^2$ is a radical selected from amino, lower alkylamino, lower cycloalkylamino, di(lower alkyl)amino, and [alpha-cyano(lower alkyl)]amino; $R^4$ is a lower alkoxy radical; and $R^6$ is a radical selected from amino, lower alkylamino, lower cycloalkylamino, and di(lower alkyl)amino; with the proviso that neither $R^2$ nor $R^6$ is tert-butylamino; and provided further that when $R^2$ is isopropylamino, $R^6$ is other than n-butylamino; and when $R^2$ is methylethylamino, $R^6$ is other than isopropylamino; and when $R^2$ is diethylamino, $R^6$ is other than amino.

Preferred active compounds result when $R^2$ is selected from lower alkylamino (except tert-butylamino) and [alpha-cyano-(lower alkyl)]amino; and $R^6$ is selected from lower alkylamino (except tert-butylamino) and lower cycloalkylamino.

Especially preferred active compounds result if $R^2$ is selected from ethylamino, isopropylamino, 1-methylpropylamino, 2-methylpropylamino, and 1-cyano-1-methylethylamino; $R^4$ is methoxy or ethoxy; and $R^6$ is selected from ethylamino, isopropylamino and cyclopropylamino.

The herbicidal compositions of this invention each contain an herbicidally effective amount of at least one active 5-pyrimidinecarbonitrile. The herbicidal compositions may take the form of granules, wettable powders, emulsifiable concentrates, solutions, or other known forms, depending on the mode of application.

The method of controlling the growth of undesired plant species within the contemplation of this invention involves applying to the area to be protected an herbicidal composition containing an herbicidally effective amount of at least one active 5-pyrimidinecarbonitrile. A variety of methods of application may be utilized and are well known in the art. These include preemergence application of an herbicidal composition to the soil before planting seeds therein or to both the soil and the seeds after the seeds are sown, as well as postemergence application to growing plants.

The synthesis of the herbicidal 5-pyrimidinecarbonitriles from 2,4,6-trichloro-5-pyrimidinecarbonitrile is described by the following chemical equations.

DETAILED DESCRIPTION OF THE INVENTION

Syntheses of the active 5-pyrimidinecarbonitriles and intermediates thereto are illustrated in the following Examples, wherein all temperatures are in degrees centigrade and pressures are in mm of mercury.

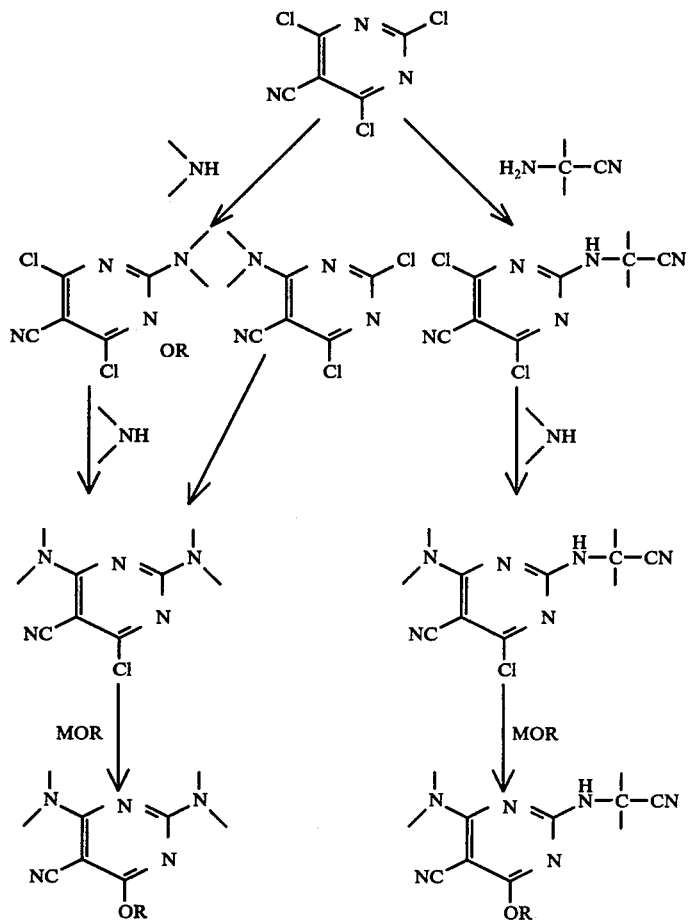

EXAMPLE I 2,4,6-Trihydroxy-5-pyrimidinecarboxamide

A mixture of 128 grams of barbituric acid and 120 grams of urea in 200 ml of 1-methyl-2-pyrrolidone was heated at 145° for 15 minutes. Hot water was then added to the reaction mixture; a white solid precipitated and was collected by filtration. The precipitate was washed with hot dimethylformamide and dried to give 165 grams of 2,4,6-trihydroxy-5-pyrimidinecarboxamide; mp, >270°. The mass spectrum of the product was consistent with the assigned structure.

EXAMPLE II 2,4,6-Trichloro-5-pyrimidinecarbonitrile

A stirred mixture of 40 grams (24 ml) of phosphorus oxychloride and 9 grams of 2,4,6-trihydroxy-5-pyrimidinecarboxamide was refluxed for 1 hour. An additional 12 ml of phosphorus oxychloride was then added, and the mixture was refluxed for an additional 3 hours. The excess phosphorus oxychloride was removed by distillation, and the residue was poured into a mixture of ice and water. The aqueous mixture was extracted with chloroform. The extract was dried with magnesium sulfate and filtered. The filtrate was evaporated under reduced pressure to a residue. The residue was sublimed to give 2 grams of 2,4,6-trichloro-5-pyrimidinecarbonitrile; mp, 117°–119°. The mass spectrum of the product was consistent with the assigned structure.

EXAMPLE III

2-Amino-2-methylpropionitrile

To a stirred solution of 54 grams of sodium cyanide in 250 ml of water at room temperature was added 73 grams of ammonium sulfate. The reaction mixture was cooled to 10°–15°, and 58 grams of acetone was added dropwise. Upon complete addition, the stirred reaction mixture was allowed to stand at room temperature for 60 hours. The organic layer was separated, and the aqueous layer was extracted with diethyl ether. The extract was combined with the organic layer, and the combination was dried over magnesium sulfate. The mixture was filtered, and the filtrate was evaporated under reduced pressure at room temperature to a residue. The residue was distilled under reduced pressure to give 24 grams of 2-amino-2-methylpropionitrile; bp, 74°–82°/70 mm. The NMR spectrum of the product was consistent with the assigned structure.

EXAMPLE IV 4,6-Dichloro-2-(1-cyano-1-methylethylamino)-5-pyrimidinecarbonitrile A stirred solution of 6.3 grams of 2,4,6-trichloro-5-pyrimidinecarbonitrile in 25 ml of acetone was cooled to −10°, and 2.5 grams of 2-amino-2-methylpropionitrile was added. With the reaction mixture at −10°, a solution of 1.3 grams of sodium hydroxide in 3.5 ml of water was added dropwise. Upon complete addition, the reaction mixture was stirred at −10° for 30 minutes. The acetone was removed under reduced pressure; the residue was extracted with diethyl ether, and the extract was separated and dried over magnesium sulfate. The extract was filtered, and the filtrate was evaporated under reduced pressure, yielding a residue. The residue was recrystallized from methylcyclohexane to give 3.1 grams of 4,6-dichloro-2-(1-cyano-1-methylethylamino)-5-pyrimidinecarbonitrile; mp, 154–158°.

Analysis: Calculated for $C_9H_7Cl_2N_5$: C,42.21; H,2.73; N,27.34; Found: C,42.26; H,2.92; N,27.35.

EXAMPLE V 4,6-Dichloro-2-ethylamino-5-pyrimidinecarbonitrile

A stirred solution of 12.9 grams of 2,4,6-trichloro-5-pyrimidinecarbonitrile in 150 ml of acetone was cooled to −10°, and 7.7 grams of an aqueous 70% ethylamine solution was added dropwise during 2 hours. The temperature of the reaction mixture was maintained at −10° throughout the addition. Following complete addition, the reaction mixture was allowed to warm to room temperature, where it stood for 16 hours. Then most of the acetone was removed by evaporation under reduced pressure. The residue was extracted with a mixture of water and diethyl ether. The ether layer was separated and dried over magnesium sulfate. The dried ether layer was filtered, and the ether was removed under reduced pressure. The residue was recrystallized from a mixture of methylcyclohexane and benzene, then from carbon tetrachloride, to give 4.2 grams of 4,6-dichloro-2-ethylamino-5-pyrimidinecarbonitrile; mp, 145–150°.

Analysis: Calculated for $C_7H_6Cl_2H_4$: C,38.74; H,2.78; N,25.80; Found: C,38.47; H,2.97; N,25.90.

EXAMPLE VI 4,6-Dichloro-2-isopropylamino-5-pyrimidinecarbonitrile

A stirred solution of 4.2 grams of 2,4,6-trichloro-5-pyrimidinecarbonitrile in 100 ml of diethyl ether was cooled to between −5° and −10°, and a solution of 2.4 grams of isopropylamine in 100 ml of diethyl ether was added dropwise. Upon complete addition, water was added to the reaction mixture, and the ether layer was separated. The ethereal layer was dried over magnesium sulfate and filtered. The filtrate was evaporated to dryness under reduced pressure. The residue was recrystallized from methylcyclohexane to give 2.4 grams of 4,6-dichloro-2-isopropylamino-5-pyrimidinecarbonitrile; mp, 179°–181°.

Analysis: Calculated for $C_8H_8Cl_2N_4$: C,41.57; H,3.47; N,24.23; Found: C,41.33; H,3.35; N,23.97.

EXAMPLE VII 4,6-Dichloro-2-(1-cyano-1-methylpropylamino)-5-pyrimidinecarbonitrile This compound was prepared in the manner of Example IV, substituting 2-amino-2-methylbutyronitrile for 2-amino-2-methylpropionitrile. The 2-amino-2-methylbutyronitrile was prepared in the manner of Example III. The reaction product was recrystallized from carbon tetrachloride to give 4,6-dichloro-2-(1-cyano-1-methylpropylamino)-5-pyrimidinecarbonitrile; mp, 130°–147°.

EXAMPLE VIII 4,6-Dichloro-2-diethylamino-5-pyrimidinecarbonitrile

A stirred solution of 6.3 grams of 2,4,6-trichloro-5-pyrimidinecarbonitrile in 150 ml of diethyl ether was cooled to −10°, and a solution of 4.4 grams of diethylamine in 75 ml of diethyl ether was added dropwise. Upon complete addition, the reaction mixture was stirred at −10° for 1 hour. Water was added to the reaction mixture. The diethyl ether layer was separated and dried over magnesium sulfate. The mixture was filtered, and the filtrate was evaporated under reduced pressure to a residue. The residue was recrystallized from methylcyclohexane to give 3.8 grams of 4,6-dichloro-2-diethylamino-5-pyrimidinecarbonitrile; mp, 125°–126°.

Analysis: Calculated for $C_9H_{10}Cl_2N_4$: C,44.10; H,4.07; N,22.85; Found: C,44.13; H,4.28; N,23.14.

EXAMPLE IX

4,6-Dichloro-2-methylamino-5-pyrimidinecarbonitrile

This compound was prepared in the manner of Example V, substituting aqueous 40% methylamine for aqueous 70% ethylamine. The reaction product was recrystallized from acetone to give 4,6-dichloro-2-methylamino-5-pyrimidinecarbonitrile; mp, 222°–225°.

Analysis:
Calculated for $C_6H_4N_4Cl_2$: C,35.50; H,1.97; N,27.60; Found: C,35.85; H,2.12; N,27.90.

EXAMPLE X

4-Chloro-2,6-bis(methylamino)-5-pyrimidinecarbonitrile

The crude reaction product of Example IX, approximately 19% 4,6-dichloro-2-methylamino-5-pyrimidinecarbonitrile and 72% 2,4-dichloro-6-methylamino-5-pyrimidinecarbonitrile, was treated with aqueous 40% methylamine in the manner of Example V, to give 4-chloro-2,6-bis(methylamino)-5-pyrimidinecarbonitrile; mp, 281°–284° C.

Analysis: Calculated for $C_7H_8ClN_5$: C,42.60; H,4.05; N,35.50; Found: C,42.80; H,4.24; N,35.44.

EXAMPLE XI

4-Chloro-2-(1-cyano-1-methylethylamino)-6-isopropylamino-5-pyrimidinecarbonitrile To a stirred solution of 5.1 grams of 4,6-dichloro-2-(1-cyano-1-methylethylamino)-5-pyrimidinecarbonitrile in 100 ml of acetone, 2.3 grams of isopropylamine was added dropwise. The reaction mixture was then stirred at room temperature for 16 hours. The acetone was removed under reduced pressure, and the reaction mixture was extracted with a mixture of diethyl ether and water. The organic layer was separated and dried over magnesium sulfate. The solution was filtered, and the filtrate was evaporated under reduced pressure, yielding a residue. The residue was recrystallized from methylcyclohexane to give 2.7 grams of 4-chloro-2-(1-cyano-1-methylethylamino)-6-isopropylamino-5-pyrimidinecarbonitrile; mp, 144°–147°.

Analysis: Calculated for $C_{12}H_{15}ClN_6$: C,51.70; H,5.42; N,30.14; Found: C,51.05; H,5.20; N,29.85.

EXAMPLE XII

4-Chloro-2-(1-cyano-1-methylpropylamino)-6-isopropylamino-5-pyrimidinecarbonitrile This compound was prepared in the manner of Example X, substituting 4,6-dichloro-2-(1-cyano-1-methylpropylamino)-5-pyrimidinecarbonitrile for 4,6-dichloro-2-(1-cyano-1-methylethylamino)-5-pyrimidinecarbonitrile, to give 4-chloro-2-(1-cyano-1-methylpropylamino)-6-isopropylamino-5-pyrimidinecarbonitrile; mp, 161°–166°.

Analysis: Calculated for $C_{13}H_{17}ClN_6$: C,53.33; H,5.85; N,28.70; Found: C,53.22; H,5.78; N,28.75.

EXAMPLE XIII

4-Chloro-6-ethylamino-2-isopropylamino-5-pyrimidinecarbonitrile

A stirred solution of 3.5 grams of 4,6-dichloro-2-isopropylamino-5-pyrimidinecarbonitrile in 100 ml of acetone was cooled to between 0° and −5°; a solution of 2.1 grams of aqueous 70% ethylamine in 25 ml of acetone was added dropwise. Upon complete addition, the reaction mixture was warmed to room temperature and stirred for 18 hours. The acetone was removed under reduced pressure, and the residue was extracted with a mixture of diethyl ether and water. The organic layer was separated and dried over magnesium sulfate. The mixture was filtered, and the filtrate was evaporated to dryness under reduced pressure. The residue was recrystallized from methylcyclohexane to give 3.1 grams of 4-chloro-6-ethylamino-2-isopropylamino-5-pyrimidinecarbonitrile; mp, 144°–146°.

Analysis: Calculated for $C_9H_{12}ClN_5$: C,47.90; H,5.35; N,31.03; Found: C,47.70; H,5.40; N,31.15.

EXAMPLE XIV

4-Chloro-2,6-bis(ethylamino)-5-pyrimidinecarbonitrile

To a stirred solution of 6.3 grams of 2,4,6-trichloro-5-pyrimidinecarbonitrile in 75 ml of acetone was added dropwise 7.7 grams of an aqueous solution of 70% ethylamine. Upon complete addition, the reaction mixture was stirred at room temperature for 60 hours. The acetone was removed by evaporation under reduced pressure. The residue was extracted with a mixture of diethyl ether and water, and 2.9 grams of insoluble 4-chloro-2,6-bis(ethylamino)-5-pyrimidinecarbonitrile, mp, 190°–191°, remained.

Analysis: Calculated for $C_9H_{12}ClN_5$: C,47.90; H,5.35; N,31.03; Found: C,47.70; H,5.40; N,31.15.

EXAMPLE XV

4-Chloro-2,6-bis(diethylamino)-5-pyrimidinecarbonitrile

To a stirred solution of 6.3 grams of 2,4,6-trichloro-5-pyrimidinecarbonitrile in 150 ml of diethyl ether at 10° was added dropwise 8.8 grams of diethylamine in 150 ml of diethyl ether. Upon complete addition, the reaction mixture was allowed to warm to room temperature, where it was stirred for 16 hours. The reaction mixture was heated under reflux for 1 hour, then cooled to room temperature. The reaction mixture was washed with water, and the diethyl ether layer was separated. The aqueous layer was washed with diethyl ether. The ether layers were combined and dried over magnesium sulfate. The mixture was filtered, and the filtrate was evaporated under reduced pressure to a residue. The residue was recrystallized from petroleum ether to give crude 4-chloro-2,6-bis(diethylamino)-5-pyrimidinecarbonitrile. This crude material was dissolved in diethyl ether, and 4.4 grams of diethylamine was added.

The reaction mixture stood at room temperature for 16 hours. The reaction mixture was washed with water, and the diethyl ether layer was separated. The ether layer was dried over magnesium sulfate and filtered. The filtrate was evaporated under reduced pressure to a residue. The residue was recrystallized from petroleum ether to give 3.2 grams of 4-chloro-2,6-bis(diethylamino)-5-pyrimidinecarbonitrile; mp, 40°–42°.

Analysis: Calculated for $C_{13}H_{20}ClN_5$: C,55.41; H,7.15; N,24.85; Found: C,55.41; H,7.39; N,25.30.

EXAMPLE XVI

4-Chloro-6-diethylamino-2-isopropylamino-5-pyrimidinecarbonitrile

To a stirred solution of 4.3 grams of 4,6-dichloro-2-isopropylamino-5-pyrimidinecarbonitrile in 125 ml of diethyl ether was added dropwise 2.6 grams of diethylamine. Upon complete addition, the reaction mixture was stirred at room temperature for 1.5 hours. The reaction mixture was washed with water. The diethyl ether layer was separated and dried over magnesium sufate. The mixture was filtered, and the filtrate was evaporated under reduced pressure to a residue. The residue was recrystallized from methylcyclohexane to give 2.5 grams of 4-chloro-6-diethylamino-2-isopropylamino-5-pyrimidinecarbonitrile; mp, 74°–76°.

Analysis: Calculated for $C_{12}H_{18}ClN_5$: C,53.83; H,6.74; N,26.15; Found: C,53.42; H,6.54; N,25.85.

EXAMPLE XVII

4-Chloro-2-ethylamino-6-isopropylamino-5-pyrimidinecarbonitrile

To a stirred solution of 6.5 grams of 4,6-dichloro-2-ethylamino-5-pyrimidinecarbonitrile in 100 ml of acetone was added dropwise 7.4 grams of isopropylamine in 30 ml of acetone. Upon complete addition, the reaction mixture was stirred at room temperature for 16 hours. The acetone was removed by evaporation under reduced pressure, and the solid residue was washed with water. The resultant solid was collected by filtration to give 6.8 grams of 4-chloro-2-ethylamino-6-isopropylamino-5-pyrimidinecarbonitrile; mp 160°–165°. Recrystallization from a mixture of benzene and methylcyclohexane gave purified product; mp, 163°–165°.

Analysis: Calculated for $C_{10}H_{14}ClN_5$: C,50.10; H,5.88; N,29.21; Found: C,49.96; H,6.15; N,29.06.

EXAMPLE XVIII

4-Chloro-2-(1-cyano-1-methylethylamino)-6-ethylamino-5-pyrimidinecarbonitrile

A stirred solution of 5.1 grams of 4,6-dichloro-2-(1-cyano-1-methylethylamino)-5-pyrimidinecarbonitrile in 50 ml of acetone was cooled to 0° to −5°, and 2.8 grams of an aqueous solution of 70% ethylamine in 40 ml of acetone was added dropwise. The temperature of the reaction mixture was maintained at 0° to −5° throughout the addition, then during 2 hours following complete addition. The reaction mixture was warmed to room temperature where it was stirred for 1 hour. Water was added to the reaction mixture, which caused precipitation of a solid. The solid was collected by filtration and recrystallized from a mixture of benzene and methylcyclohexane to give 3.3 grams of 4-chloro-2-(1-cyano-1-methylethylamino)-6-ethylamino-5-pyrimidinecarbonitrile; mp, 157°–160°.

Analysis: Calculated for $C_{11}H_{13}ClN_6$: C,50.59; H,5.18; N,31.55; Found: C,50.61; H,4.88; N,31.80.

EXAMPLE XIX

4-Chloro-6-isopropylamino-2-methylamino-5-pyrimidinecarbonitrile

This compound was prepared in the manner of Example XVII, substituting 4,6-dichloro-2-methylamino-5-pyrimidinecarbonitrile for 4,6-dichloro-2-ethylamino-5-pyrimidinecarbonitrile. The reaction product was recrystallized from benzene to give 4-chloro-6-isopropylamino-2-methylamino-5-pyrimidinecarbonitrile; mp, 218°–220°.

Analysis: Calculated for $C_9H_{12}ClN_5$: C,47.90; H,5.36; N,31.03; Found: C,47.47; H,5.33; N,31.94.

EXAMPLE XX

4-Chloro-2-isopropylamino-6-methylamino-5-pyrimidinecarbonitrile

This compound was prepared in the manner of Example XVII, substituting 4,6-dichloro-2-isopropylamino-5-pyrimidinecarbonitrile and aqueous 40% methylamine for 4,6-dichloro-2-ethylamino-5-pyrimidinecarbonitrile and isopropylamine. The reaction product was recrystallized from methylcyclohexane to give 4-chloro-2-isopropylamino-6-methylamino-5-pyrimidinecarbonitrile; mp, 170°–173°.

Analysis:
Calculated for $C_9H_{12}ClN_5$: C,47.90; H,5.36; N,31.03; Found: C,48.12; H,5.59; N,31.10.

EXAMPLE XXI

4-Chloro-6-diethylamino-2-ethylamino-5-pyrimidinecarbonitrile

This compound was prepared in the manner of Example XVII, substituting diethylamine for isopropylamine. The product was 4-chloro-6-diethylamino-2-ethylamino-5-pyrimidinecarbonitrile; mp, 144°–146°.

Analysis: Calculated for $C_{11}H_{15}ClN_5$: C,52.28; H,5.98; N,27.71; Found: C,52.05; H,6.09; N,27.93.

EXAMPLE XXII

4-Chloro-2-(1-cyano-1-methylethylamino)-6-(1-methylbutylamino)-5-pyrimidinecarbonitrile This compound was prepared in the manner of Example X, substituting 2-aminopentane for isopropylamine. The reaction product was recrystallized from a mixture of benzene and methylcyclohexane to give 4-chloro-2-(1-cyano-1-methylethylamino)-6-(1-methylbutylamino)-5-pyrimidinecarbonitrile; mp, 133°–135°.

Analysis: Calculated for $C_{14}H_{19}C,N_6$: C,54.80; H,6.24; N,27.39; Found: C,54.91; H,6.41; N,27.59.

EXAMPLE XXIII

4-Chloro-2-(1-cyano-1-methylethylamino)-6-(1-isopropyl-2-methylpropylamino)-5-pyrimidinecarbonitrile This compound was prepared in the manner of Example X, substituting 1-isopropyl-2-methylpropylamine for isopropylamine. The reaction product was recrystallized from a mixture of benzene and methylcyclohexane to give 4-chloro-2-(1-cyano-1-methylethylamino)-6-(1-isopropyl-2-methylpropylamino)-5-pyrimidinecarbonitrile; mp, 146°–150°.

Analysis: Calculated for $C_{16}H_{23}ClN_6$: C,57.38; H,6.92; N,25.10; Found: C,57.05; H,6.30; N,25.38.

EXAMPLE XXIV

4-Chloro-2-(1-cyano-1-methylethylamino)-6-cyclopropylamino-5-pyrimidinecarbonitrile This compound was prepared in the manner of Example X, substituting cyclopropylamine for isopropylamine. The reaction product was recrystallized from a mixture of benzene and methylcyclohexane to give 4-chloro-2-(1-cyano-1-methylethylamino)-6-cyclopropylamino-5-pyrimidinecarbonitrile; mp, 174°–177°.

Analysis: Calculated for $C_{12}H_{13}ClN_6$: C,52.08; H,4.73; N,30.35; Found: C,51.98; H,5.00; N,30.41.

EXAMPLE XXV

6-Amino-4-chloro-2-(1-cyano-1-methylethylamino)-5-pyrimidinecarbonitrile

This compound was prepared in the manner of Example X, substituting aqueous 29.8% ammonium hydroxide for isopropylamine. The reaction product was recrystallized from benzene to give 6-amino-4-chloro-2-(1-cyano-1-methylethylamino)-5-pyrimidinecarbonitrile; mp, 193°–198°.

Analysis: Calculated for $C_9H_9ClN_6$: C,45.67; H,3.83; N,35.51; Found: C,45.66; H,4.07; N,35.57.

EXAMPLE XXVI

6-Butylamino-4-chloro-2-(1-cyano-1-methylethylamino)-5-pyrimidinecarbonitrile This compound was prepared in the manner of Example X, substituting n-butylamine for isopropylamine. The reaction product was recrystallized from methylcyclohexane to give 6-butylamino-4-chloro-2-(1-cyano-1-methylethylamino)-5-pyrimidinecarbonitrile; mp, 129°–134°.

Analysis: Calculated for $C_{13}H_{17}ClN_6$: C,53.33; H,5.85; N,28.70; Found: C,53.62; H,5.98; N,28.77.

EXAMPLE XXVII

4-Chloro-2-(1-cyano-1-methylpropylamino)-6-cyclopropylamino-5-pyrimidinecarbonitrile This compound was prepared in the manner of Example X, substituting 4,6-dichloro-2-(1-cyano-1-methylpropylamino)-5-pyrimidinecarbonitrile and cyclopropylamine for 4,6-dichloro-2-(1-cyano-1-methylethylamino)-5-pyrimidinecarbonitrile and isopropylamine. The reaction product was recrystallized from carbon tetrachloride to give 4-chloro-2-(1-cyano-1-methylpropylamino)-6-cyclopropylamino-5-pyrimidinecarbonitrile; mp, 155°–159°.

Analysis: Calculated for $C_{13}H_{15}ClN_6$: C,53.70; H,5.20; N,28.90; Found: C,53.10; H,5.17; N,29.28.

EXAMPLE XXVIII

6-Amino-4-chloro-2-isopropylamino-5-pyrimidinecarbonitrile

This compound was prepared in the manner of Example XVII, substituting 4,6-dichloro-2-isopropylamino-5-pyrimidinecarbonitrile and aqueous ammonia for 4,6-dichloro-2-ethylamino-5-pyrimidinecarbonitrile and isopropylamine. The reaction product was recrystallized from benzene to give 6-amino-4-chloro-2-isopropylamino-5-pyrimidinecarbonitrile; mp, 162°–165°.

Analysis: Calculated for $C_8H_{10}ClN_5$: C,45.39; H,4.76; N,33.08; Found: C,45.71; H,4.94; N,32.88.

EXAMPLE XXIX

4-Chloro-6-cyclopropylamino-2-isopropylamino-5-pyrimidinecarbonitrile

This compound was prepared in the manner of Example XVII, substituting 4,6-dichloro-2-isopropylamino-5-pyrimidinecarbonitrile and cyclopropylamine for 4,6-dichloro-2-ethylamino-5-pyrimidinecarbonitrile and isopropylamine, producing 4-chloro-6-cyclopropylamino-2-isopropylamino-5-pyrimidinecarbonitrile. Upon recrystallization from methylcyclohexane, the melting point was 157°–160°.

Analysis: Calculated for $C_{11}H_{14}ClN_5$: C,52.66; H,5.71; N,27.87; Found: C,52.57; H,5.71; N,27.84.

EXAMPLE XXX

4-Chloro-6-cyclopropylamino-2-diethylamino-5-pyrimidinecarbonitrile

To a stirred solution of 6.9 grams of 4,6-dichloro-2-diethylamino-5-pyrimidinecarbonitrile in 80 ml of acetone was added dropwise 3.2 grams of cyclopropylamine in 20 ml of acetone. The reaction mixture stood for 16 hours; then the acetone was removed by evaporation under reduced pressure. The residue was washed with water, and the resultant solid was collected. The solid was washed several times with water, then dried, to give 6.5 grams of crude product; mp, 100°–105°. The crude product was recrystallized from petroleum ether to give 2.5 grams of 4-chloro-6-cyclopropylamino-2-diethylamino-5-pyrimidinecarbonitrile; mp, 120°–122°.

Analysis: Calculated for $C_{12}H_{16}ClN_5$: C,54.23; H,6.06; N,26.35; Found: C,54.12; H,5.99; N,26.43.

EXAMPLE XXXI

4-Chloro-6-ethylamino-2-methylamino-5-pyrimidinecarbonitrile

This compound was prepared in the manner of Example XVII, substituting 4,6-dichloro-2-methylamino-5-pyrimidinecarbonitrile and aqueous 70% ethylamine for 4,6-dichloro-2-ethylamino-5-pyrimidinecarbonitrile and isopropylamine. The product was 4-chloro-6-ethylamino-2-methylamino-5-pyrimidinecarbonitrile; mp, 155°–158°.

Analysis: Calculated for $C_8H_{10}ClN_5$: C,45.5p; H<5>13; N,33.20; Found: C,45.22; H,4.80; N,33.50.

EXAMPLE XXXII

4-Chloro-2,6-bis(isopropylamino)-5-pyrimidinecarbonitrile

This compound was prepared in the manner of Example XV, substituting isopropylamine for diethylamine. The reaction product was recrystallized from methylcyclohexane to give 4-chloro-2,6-bis(isopropylamino)-5-pyrimidinecarbonitrile; mp, 161°–162° C.

Analysis: Calculated for $C_{11}H_{16}ClN_5$: C,52.07; H,6.35; N,27.60; Found: C,52.04; H,6.69; N,27.45.

EXAMPLE XXXIII

2-(1-Cyano-1-methylethylamino)-6-ethylamino-4-methoxy-5-pyrimidinecarbonitrile To a stirred solution of 2.7 grams of 4-chloro-2-(1-cyano-1-methylethylamino)-6-ethylamino-5-pyrimidinecarbonitrile in 50 ml of methanol was added a solution of 0.3 gram of sodium in 10 ml of methanol. The reaction mixture was heated under reflux for 3 hours. An additional small quantity of sodium in methanol was then added to the reaction mixture, and heating under reflux was continued for 1.5 hours. The excess methanol was removed from the reaction mixture by evaporation under reduced pressure. The residue was extracted with a mixture of diethyl ether and water. The diethyl ether layer was separated, washed with water, then dried over magnesium sulfate. The mixture was filtered, and the filtrate was evaporated under reduced pressure to a residue. The residue was washed with methylcyclohexane, and the insoluble solid was collected by filtration. The solid was recrystallized from benzene to give 1.7 grams of 2-(1-cyano-1-methylethylamino)-6-ethylamino-4-methoxy-5-pyrimidinecarbonitrile; mp, 130°–132°.

Analysis: Calculated for $C_{12}H_{16}N_6O$: C,55.37; H,6.20 N,32.29; Found: C,55.68; H,6.48; N,32.23.

EXAMPLE XXXIV 2-(1-Cyano-1-methylpropylamino)-6-isopropylamino-4-methoxy-5-pyrimidinecarbonitrile This compound was prepared in the manner of Example XXXIII substituting 4-chloro-2-(1-cyano-1-methylpropylamino)-6-isopropylamino-5-pyrimidinecarbonitrile for 4-chloro-2-(1-cyano-1-methylethylamino)-6-ethylamino-5-pyrimidinecarbonitrile. The reaction product was recrystallized from a mixture of benzene and hexane to give 2-(1-cyano-1-methylpropylamino)-6-isopropylamino-4-methoxy-5-pyrimidinecarbonitrile; mp, 145°-146°.

Analysis: Calculated for $C_{14}H_{20}N_6O$: C,58.31; H,6.99; N,29.14; Found: C,58.19; H,6.64; N,28.72.

EXAMPLE XXXV 2-(1-Cyano-1-methylethylamino)-6-isopropylamino-4-methoxy-5-pyrimidinecarbonitrile A solution of 3.8 grams of 4-chloro-2-(1-cyano-1-methylethylamino)-6-isopropylamino-5-pyrimidinecarbonitrile in methanol was added to a solution of 0.3 gram of sodium in 20 ml of methanol. The reaction mixture was heated under reflux for 4 hours, then allowed to stand at room temperature for 60 hours. The solution resulting from the addition of 0.05 gram of sodium to 5 ml of methanol was added to the reaction mixture. The reaction mixture was then heated under reflux for 3 hours.

The excess methanol was removed under reduced pressure, and the residue was extracted with a mixture of diethyl ether and water. The ether layer was separated and dried over magnesium sulfate. The mixture was filtered, and the filtrate was evaporated to dryness under vacuum. The residue was recrystallized from a mixture of benzene and petroleum ether to give 1.1 grams of 2-(1-cyano-1-methylethylamino)-6-isopropylamino-4-methoxy-5-pyrimidinecarbonitrile; mp, 156°-159°.

Analysis: Calculated for $C_{13}H_{18}N_6O$: C,56.92; H,6.61; N,30.64; Found: C,57.10; H,6.70; N,30.90.

EXAMPLE XXXVI

6-Ethylamino-2-isopropylamino-4-methoxy-5-pyrimidinecarbonitrile

This compound was prepared in the manner of Example XXXIII, substituting 4-chloro-6-ethylamino-2-isopropylamino-5-pyrimidinecarbonitrile for 4-chloro-2-(1-cyano-1-methylethylamino)-6-ethylamino-5-pyrimidinecarbonitrile. The reaction product was recrystallized from methylcyclohexane, to give 6-ethylamino-2-isopropylamino-4-methoxy-5-pyrimidinecarbonitrile; mp, 124°-126°.

Analysis: Calculated for $C_{11}H_{17}N_5O$: C,56.15; H,7.28; N,29.77; Found: C,55.87; H,7.16; N,28.99.

EXAMPLE XXXVII 2,6-Bis(ethylamino)-4-methoxy-5-pyrimidinecarbonitrile

This compound was prepared in the manner of Example XXXIII, substituting 4-chloro-2,6-bis(ethylamino)-5-pyrimidinecarbonitrile for 4-chloro-2-(1-cyano-1-methylethylamino)-6-ethylamino-5-pyrimidinecarbonitrile. The reaction product was recrystallized from a mixture of benzene and petroleum ether, to give 2,6-bis(ethylamino)-4-methoxy-5-pyrimidinecarbonitrile; mp, 114°-116°.

Analysis: Calculated for $C_{10}H_{15}N_5O$: C,54.28; H,6.83; N,31.66; Found: C,54.38; H,7.08; N,31.93.

EXAMPLE XXXVIII 2,6-Bis(diethylamino)-4-methoxy-5-pyrimidinecarbonitrile

This compound was prepared in the manner of Example XXXIII, substituting 4-chloro-2,6-bis(diethylamino)-5-pyrimidinecarbonitrile for 4-chloro-2-(1-cyano-1-methylethylamino)-6-ethylamino-5-pyrimidinecarbonitrile. The reaction product was recrystallized from petroleum ether to give 2,6-bis(diethylamino)-4-methoxy-5-pyrimidinecarbonitrile; mp, 37°-39°.

Analysis: Calculated for $C_{14}H_{23}N_5O$: C,60.62; H,8.36; N,25.25; Found: C,60.92; H,8.40; N,25.60.

EXAMPLE XXXIX

6-Diethylamino-2-isopropylamino-4-methoxy-5-pyrimidinecarbonitrile

This compound was prepared in the manner of Example XXXV, substituting 4-chloro-6-diethylamino-2-isopropylamino-5-pyrimidinecarbonitrile for 4-chloro-2-(1=cyano-1-methylethylamino)-6-isopropylamino-5-pyrimidinecarbonitrile. It yielded liquid 6-diethylamino-2-isopropylamino-4-methoxy-5-pyrimidinecarbonitrile.

Analysis: Calculated for $C_{13}H_{21}N_5O$: C,59.29; H,8.04; N,26.60; Found: C,59.00; H,8.33; N,26.36.

EXAMPLE XL

2-Ethylamino-6-isopropylamino-4-methoxy-5-pyrimidinecarbonitrile

This compound was prepared in the manner of Example XXXV, substituting 4-chloro-2-ethylamino-6-isopropylamino-5-pyrimidinecarbonitrile for 4-chloro-2-(1-cyano-1-methylethylamino)-6-isopropylamino-5-pyrimidinecarbonitrile. The product was 2-ethylamino-6-isopropylamino-4-methoxy-5-pyrimidinecarbonitrile; mp, 125°-128°.

Analysis: Calculated for $C_{11}H_{17}N_5O$: C,56.15; H,7.28; N,29.76; Found: C,56.12; H,6.99; N,29.75.

EXAMPLE XLI

4-Ethoxy-6-ethylamino-2-isopropylamino-5-pyrimidinecarbonitrile

This compound was prepared in the manner of Example XXXIII, substituting 4-chloro-6-ethylamino-2-isopropylamino-5-pyrimidinecarbonitrile and a solution of sodium in ethanol for 4-chloro-2-(1-cyano-1-methylethylamino)-6-ethylamino-5-pyrimidinecarbonitrile and a solution of sodium in methanol. The reaction product was recrystallized from petroleum ether to give 4-ethoxy-6-ethylamino-2-isopropylamino-5-pyrimidinecarbonitrile; mp, 98°-99°.

Analysis: Calculated for $C_{12}H_{19}N_5O$: C,57.81; H,7.68; N,28.09; Found: C,57.89; H,7.59; N,28.18.

EXAMPLE XLII

6-Ethylamino-4-methoxy-2-methylamino-5-pyrimidinecarbonitrile

This compound was prepared in the manner of Example XXXV, substituting 4-chloro-6-ethylamino-2- methylamino-5-pyrimidinecarbonitrile for 4-chloro-2-(1-cyano-1-methylethylamino)-6-isopropylamino-5-pyrimidinecarbonitrile. The product was 6-ethylamino-4-methoxy-2-methylamino-5-pyrimidinecarbonitrile; mp, 147°–149°.

Analysis: Calculated for $C_9H_{13}N_5O$: C,52.16; H,6.32; N,33.80; Found: C,52.08; H,6.60; N,34.07.

EXAMPLE XLIII

6-Isopropylamino-4-methoxy-2-methylamino-5-pyrimidinecarbonitrile

This compound was prepared in the manner of Example XXXV, substituting 4-chloro-6-isopropylamino-2-methylamino-5-pyrimidinecarbonitrile for 4-chloro-2-(1-cyano-1-methylethylamino)-6-isopropylamino-5-pyrimidinecarbonitrile. The product was 6-isopropylamino-4-methoxy-2-methylamino-5-pyrimidinecarbonitrile; mp, 112°–115°.

Analysis: Calculated for $C_{10}H_{15}N_5O$: C,54.28; H,6.83; N,31.66; Found: C,53.14; H,6.61; N,32.26.

EXAMPLE XLIV

2-Isopropylamino-4-methoxy-6-methylamino-5-pyrimidinecarbonitrile

This compound was prepared in the manner of Example XXXV, substituting 4-chloro-2-isopropylamino-6-methylamino-5-pyrimidinecarbonitrile for 4-chloro-2-(1-cyano-1-methylethylamino)-6-isopropylamino-5-pyrimidinecarbonitrile. The product was 2-isopropylamino-4-methoxy-6-methylamino-5-pyrimidinecarbonitrile; mp, 134°–137°.

Analysis: Calculated for $C_{10}H_{15}N_5O$: C,54.28; H,6.83; N,31.66; Found: C,53.63; H,6.50; N,31.88.

EXAMPLE XLV

6-Diethylamino-2-ethylamino-4-methoxy-5-pyrimidinecarbonitrile

This compound was prepared in the manner of Example XXXV, substituting 4-chloro-6-diethylamino-2-ethylamino-5-pyrimidinecarbonitrile for 4-chloro-2-(1-cyano-1-methylethylamino)-6-isopropylamino-5-pyrimidinecarbonitrile. The product was 6-diethylamino-2-ethylamino-4-methoxy-5-pyrimidinecarbonitrile; mp, 73°–75°.

Analysis: Calculated for $C_{12}H_{18}N_5O$: C,57.81; H,7.68; N,28.09; Found: C,57.67; H,7.46; N,28.26.

EXAMPLE XLVI

4-Ethoxy-6-diethylamino-2-isopropylamino-5-pyrimidinecarbonitrile

This compound was prepared in the manner of Example XXXIII, substituting 4-chloro-6-diethylamino-2-isopropylamino-5-pyrimidinecarbonitrile and a solution of sodium in ethanol for 2-(1-cyano-1-methylethylamino)-6-ethylamino-5-pyrimidinecarbonitrile and a solution of sodium in methanol. The reaction product was recrystallized from hexane to give 4-ethoxy-6-diethylamino-2-isopropylamino-5-pyrimidinecarbonitrile; mp, 55°–57°.

Analysis: Calculated for $C_{14}H_{23}N_5O$: C,60.62; H,8.36; N,25.25; Found: C,60.32; H,8.33; N,25.30.

EXAMPLE XLVII

2-(1-Cyano-1-methylethylamino)-4-methoxy-6-(1-methylbutylamino)-5-pyrimidinecarbonitrile This compound was prepared in the manner of Example XXXV, substituting 4-chloro-2-(1-cyano-1-methylethylamino)-6-(1-methylbutylamino)-5-pyrimidinecarbonitrile for 4-chloro-2-(1-cyano-1-methylethylamino)-6-isopropylamino-5-pyrimidinecarbonitrile. The reaction product was recrystallized twice from methylcyclohexane to give 2-(1-cyano-1-methylethylamino)-4-methoxy-6-(1-methylbutylamino)-5-pyrimidinecarbonitrile; mp, 142°–147°.

Analysis: Calculated for $C_{15}H_{22}N_6O$: C,59.58; H,7.33; N,27.80; Found: C,59.43; H,7.59; N,27.75.

EXAMPLE XLVIII

2-(1-Cyano-1-methylethylamino)-6-(1-isopropyl-2-methylpropylamino)-4-methoxy-5-pyrimidinecarbonitrile This compound was prepared in the manner of Example XXXV, substituting 4-chloro-2-(1-cyano-1-methylethylamino)-6-(1-isopropyl-2-methylpropylamino)-5-pyrimidinecarbonitrile for 4-chloro-2-(1-cyano-1-methylethylamino)-6-isopropylamino-5-pyrimidinecarbonitrile. The reaction product was recrystallized from methylcyclohexane to give 2-(1-cyano-1-methylethylamino)-6-(1-isopropyl-2-methylpropylamino)-4-methoxy-5-pyrimidinecarbonitrile; mp, 121°–124°.

Analysis: Calculated for $C_{17}H_{26}N_6O$: C,61.79; H,7.93; N,25.44; Found: C,61.49; H,7.73; N,25.67.

EXAMPLE XLIX

2-(1-Cyano-1-methylethylamino)-6-cyclopropylamino-4-methoxy-5-pyrimidinecarbonitrile To a stirred solution of 0.8 gram of sodium methoxide in 100 ml of methanol was added portionwise 4.2 grams of 4-chloro-2-(1-cyano-1-methylethylamino)-6-cyclopropylamino-5-pyrimidinecarbonitrile. Upon complete addition, the reaction mixture was heated under reflux for 3.5 hours, then allowed to stand at room temperature for 16 hours. The methanol was removed by evaporation under reduced pressure. The residue was extracted with a mixture of water and methylene chloride. The methylene chloride layer was separated and dried over magnesium sulfate. The mixture was filtered, and the filtrate was evaporated under reduced pressure. The residue was recrystallized twice from carbon tetrachloride to give 2.4 grams of 2-(1-cyano-1-methylethylamino)-6-cyclopropylamino-4-methoxy-5-pyrimidinecarbonitrile; mp, 138°–140°.

Analysis: Calculated for $C_{13}H_{16}N_6O$: C,57.33; H,5.93; N,30.86; Found: C,57.21; H,5.99; N,30.84.

EXAMPLE L

6-Amino-2-(1-cyano-1-methylethylamino)-4-methoxy-5-pyrimidinecarbonitrile

This compound was prepared in the manner of Example XXXIII, substituting 6-amino-4-chloro-2-(1-cyano-1-methylethylamino)-5-pyrimidinecarbonitrile for 4-chloro-2-(1-cyano-1-methylethylamino)-6-ethylamino-5-pyrimidinecarbonitrile. The reaction product was recrystallized from anhydrous ethanol to give 6-amino-2-(1-cyano-1-methyethylamino)-4-methoxy-5-pyrimidinecarbonitrile; mp, 240°–243°.

Analysis: Calculated for $C_{10}H_{12}N_6O$: C,51.71; H,5.21; N,36.19; Found: C,51.70; H,5.51; N,36.47.

EXAMPLE LI

6-Butylamino-2-(1-cyano-1-methylethylamino)-4-methoxy-5-pyrimidinecarbonitrile

This compound was prepared in the manner of Example XXXV, substituting 6-butylamino-4-chloro-2-(1-cyano-1-methylethylamino)-5-pyrimidinecarbonitrile for 4-chloro-2-(1-cyano-1-methylethylamino)-6-isopropylamino-5-pyrimidinecarbonitrile. The reaction product was recrystallized from methylcyclohexane to give 6-butylamino-2-(1-cyano-1-methylethylethylamino)-4-methoxy-5-pyrimidinecarbonitrile; mp, 120°–127°.

Analysis: Calculated for $C_{14}H_{20}N_6O$: C,58.31; H,6.99; N,29.14; Found: C,57.87; H,6.69; N,29.48.

EXAMPLE LII 2-(1-Cyano-1-methylpropylamino)-6-cyclopropylamino-4-methoxy-5-pyrimidinecarbonitrile This compound was prepared in the manner of Example XXXV, substituting 4-chloro-2-(1-cyano-1-methylpropylamino)-6-cyclopropylamino-5-pyrimidinecarbonitrile for 4-chloro-2-(1-cyano-1-methylethylamino)-6-isopropylamino-5-pyrimidinecarbonitrile. The reaction product was recrystallized from a mixture of benzene and methylcyclohexane to give 2-(1-cyano-1-methylpropylamino)-6-cyclopropylamino-4-methoxy-5-pyrimidinecarbonitrile; mp, 114°–118°.

Analysis: Calculated for $C_{14}H_{18}N_6O$: C,58.73; H,6.34; N,29.35; Found: C,58.70; H,6.55; N,29.35.

EXAMPLE LIII

6-Amino-2-isopropylamino-4-methoxy-5-pyrimidinecarbonitrile

This compound was prepared in the manner of Example XXXV, substituting 6-amino-4-chloro-2-isopropylamino-5-pyrimidinecarbonitrile for 4-chloro-2-(1-cyano-1-methylethylamino)-6-isopropylamino-5-pyrimidinecarbonitrile. The product was 6-amino-2-isopropylamino-4-methoxy-5-pyrimidinecarbonitrile; mp, 224°–227°.

Analysis: Calculated for $C_9H_{13}N_5O$: C,52.16; H,6.32; N,33.80; Found: C,51.80; H,6.39; N,33.87.

EXAMPLE LIV

6-Cyclopropylamino-2-isopropylamino-4-methoxy-5-pyrimidinecarbonitrile

To a stirred solution of 0.9 gram of sodium methoxide in 100 ml of methanol was added, in one portion, 4.0 grams of 4-chloro-6-cyclopropylamino-2-isopropylamino-5-pyrimidinecarbonitrile. The reaction mixture was then heated under reflux for 3 hours. The methanol was removed by evaporation under reduced pressure to give a residue. The residue was washed with water, and the solid was collected by filtration to yield 3.5 grams of 6-cyclopropylamino-2-isopropylamino-4-methoxy-5-pyrimidinecarbonitrile; mp, 142°–147°.

Analysis: Calculated for $C_{12}H_{17}N_5O$: C,58.28; H,6.92; N,28.31; Found: C,58.04; H,6.98; N,28.34.

EXAMPLE LV

6-Cyclopropylamino-2-diethylamino-4-methoxy-5-pyrimidinecarbonitrile

This compound was prepared in the manner of Example XXXV, substituting 4-chloro-6-cyclopropylamino-2-diethylamino-5-pyrimidinecarbonitrile for 4-chloro-2-(1-cyano-1-methylethylamino)-6-isopropylamino-5-pyrimidinecarbonitrile, to produce 6-cyclopropylamino-2-diethylamino-4-methoxy-5-pyrimidinecarbonitrile. Upon recrystallization from methylcyclohexane, the melting point was 146°–150°.

Analysis: Calculated for $C_{13}H_{14}N_5O$: C,59.15; H,7.33; N,26.80; Found: C,59.02; H,7.05; N,26.79.

EXAMPLE LVI 2,6-Bis(isopropylamino)-4-methoxy-5-pyrimidinecarbonitrile

To a solution of 6.3 grams of 4-chloro-2,6-bis(isopropylamino)-5-pyrimidinecarbonitrile in 100 ml of methanol was added a solution of methanolic sodium methoxide (0.805 grams of sodium in 50 ml of methanol). After complete addition, the reaction mixture was stirred for 16 hours. The reaction mixture was then heated under reflux for 5 hours. The excess methanol was removed under reduced pressure. The residue was extracted with a mixture of diethyl ether and water. The organic layer was separated and dried over magnesium sulfate. The mixture was filtered, and the filtrate was evaporated to dryness under reduced pressure. The residue was recrystallized from cyclohexane, to give 4.5 grams of 2,6-bis(isopropylamino)-4-methoxy-5-pyrimidinecarbonitrile; mp, 131°–133°.

Analysis: Calculated for $C_{12}H_{19}N_5O$: C,57.81; H,7.68; N,28.09; Found: C,57.57; H,7.62; N,28.15.

EXAMPLE LVII

4-Methoxy-2,6-bis(methylamino)-5-pyrimidinecarbonitrile

This compound, mp, 177°–179°, was prepared by the method of Example XXXV, substituting 4-chloro-2,6-bis(methylamino)-5-pyrimidinecarbonitrile for 4-chloro-2-(1-cyano-1-methylethylamino)-6-isopropylamino-5-pyrimidinecarbonitrile.

EXAMPLE LVIII

2-Cyclopropylamino-6-isopropylamino-4-methoxy-5-pyrimidinecarbonitrile

4-Chloro-2-cyclopropylamino-6-isopropylamino-5-pyrimidinecarbonitrile was prepared by the method of Example XVII, substituting 2,4-dichloro-6-isopropylamino-5-pyrimidinecarbonitrile (isolated from a mixture of 2,4-dichloro-6-isopropylamino-5-pyrimidinecarbonitrile and 4,6-dichloro-2-isopropylamino-5-pyrimidinecarbonitrile), and cyclopropylamine for 4,6-dichloro-2-ethylamino-5-pyrimidinecarbonitrile and isopropylamine. The reaction product was recrystallized from benzene to give 4-chloro-2-cyclopropylamino-6-isopropylamino-5-pyrimidinecarbonitrile; mp, 212°–215°.

Analysis: Calculated for $C_{11}H_{14}ClN_5$: C,52.48; H,5.61; N,27.82; Found: C,52.69; H,5.77; N,28.05.

2-Cyclopropylamino-6-isopropylamino-4-methoxy-5-pyrimidinecarbonitrile was then prepared by the method of Example LIV, substituting 4-chloro-2-cyclopropylamino-6-isopropylamino-5-pyrimidinecarbonitrile for 4-chloro-6-cyclopropylamino-2-isopropylamino-5-pyrimidinecarbonitrile. The reaction product was recrystallized from methylcyclohexane to give 2-cyclopropylamino-6-isopropylamino-4-methoxy-5-pyrimidinecarbonitrile; mp, 108°–111°.

Analysis: Calculated for $C_{12}H_{17}N_5O$: C,58.28; H,6.93; N,28.32; Found: C,58.70; H,6.78; N,28.66.

EXAMPLE LIX

2,6-Bis(cyclopropylamino)-4-methoxy-5-pyrimidinecarbonitrile

4-Chloro-2,6-bis(cyclopropylamino)-5-pyrimidinecarbonitrile was prepared by the method of Example XIV, substituting cyclopropylamine for 70% ethylamine. The reaction product was recrystallized from a mixture of benzene and methylcyclohexane to give 4-chloro-2,6-bis(cyclopropylamino)-5-pyrimidinecarbonitrile; mp, 210°–215°.

Analysis: Calculated for $C_{11}H_{12}ClN_5$: C,52.91; H,4.84; N,28.04; Found: C,52.53; H,4.99; N,27.67.

2,6-Bis(cyclopropylamino)-4-methoxy-5-pyrimidinecarbonitrile was then prepared by the method of Example LIV, substituting 4-chloro-2,6-bis(cyclopropylamino)-5-pyrimidinecarbonitrile for 4-chloro-6-cyclopropylamino-2-isopropylamino-5-pyrimidinecarbonitrile. The reaction product was recrystallized from methylcyclohexane to give 2,6-bis(cyclopropylamino)-4-methoxy-5-pyrimidinecarbonitrile; mp, 130°–135°.

Analysis: Calculated for $C_{12}H_{15}N_5O$: C,58.76; H,6.16; N,28.56; Found: C,58.71; H,6.53; N,28.75.

EXAMPLE LX

6-Cyclopropylamino-4-methoxy-2-(1-methylpropylamino)-5-pyrimidinecarbonitrile 4,6-Dichloro-2-(1-methylpropylamino)-5-pyrimidinecarbonitrile was prepared by the method of Example V, substituting 1-methylpropylamine for 70% ethylamine. The reaction product was recrystallized from methylcyclohexane, then from a mixture of benzene and hexane to give 4,6-dichloro-2-(1-methylpropylamino)-5-pyrimidinecarbonitrile; mp, 110°–120°.

Analysis: Calculated for $C_9H_{10}Cl_2N_4$: C,44.10; H,4.11; N,22.86; Found: C,44.34; H,4.43; N,22.88.

4-Chloro-6-cyclopropylamino-2-(1-methylpropylamino)-5-pyrimidinecarbonitrile was prepared by the method of Example XVII, substituting 4,6-dichloro-2-(1-methylpropylamino)-5-pyrimidinecarbonitrile and cyclopropylamine for 4,6-dichloro-2-ethylamino-5-pyrimidinecarbonitrile and isopropylamine. The reaction product was recrystallized from methylcyclohexane to give 4-chloro-6-cyclopropylamino-2-(1-methylpropylamino)-5-pyrimidinecarbonitrile; mp, 112°–114°.

Analysis: Calculated for $C_{12}H_{16}ClN_5$: C,54.23; H,6.07; N,26.35; Found: C,54.13; H,6.25; N,26.38.

6-Cyclopropylamino-4-methoxy-2-(1-methylpropylamino)-5-pyrimidinecarbonitrile was prepared in the manner of Example LIV, substituting 4-chloro-6-cyclopropylamino-2-(1-methylpropylamino)-5-pyrimidinecarbonitrile for 4-chloro-6-cyclopropylamino-2-isopropylamino-5-pyrimidinecarbonitrile. The reaction product was recrystallized from methylcyclohexane to give 6-cyclopropylamino-4-methoxy-2-(1-methylpropylamino)-5-pyrimidinecarbonitrile; mp, 120°–123°.

Analysis: Calculated for $C_{13}H_{19}N_5O$: C,59.75; H,7.33; N,26.80; Found: C,59.26; H,7.39; N,26.61.

EXAMPLE LXI

4-Methoxy-6-(1-methylethylamino)-2-(2-methylpropylamino)-5-pyrimidinecarbonitrile 4,6-Dichloro-2-(2-methylpropylamino)-5-pyrimidinecarbonitrile was prepared by the method of Example V, substituting 2-methylpropylamine for 70% ethylamine. The reaction product was recrystallized from a mixture of benzene and methylcyclohexane to give 4,6-dichloro-2-(2-methylpropylamino)-5-pyrimidinecarbonitrile; mp, 137°–150°.

Analysis: Calculated for $C_9H_{10}Cl_2N_4$: C,44.10; H,4.11; N,22.86; Found: C,43.62; H, 4.08; N,22.67.

4-Chloro-6-(1-methylethylamino)-2-(2-methylpropylamino)-5-pyrimidinecarbonitrile was prepared by the method of Example XVII, substituting 4,6-dichloro-2-(2-methylpropylamino)-5-pyrimidinecarbonitrile for 4,6-dichloro-2-ethylamino-5-pyrimidinecarbonitrile. The reaction product was recrystallized from methylcyclohexane to give 4-chloro-6-(1-methylethylamino)-2-(2-methylpropylamino)-5-pyrimidinecarbonitrile; mp, 170°–172°.

Analysis: Calculated for $C_{12}H_{18}ClN_5$: C,53.82; H,6.77; N,26.16; Found: C,53.79; H,6.95; N,26.41.

4-Methoxy-6-(1-methylethylamino)-2-(2-methylpropyl-amino)-5-pyrimidinecarbonitrile was prepared in the manner of Example LIV, substituting 4-chloro-6-(1-methylethylamino)-2-(2-methylpropylamino)-5-pyrimidinecarbonitrile for 4-chloro-6-cyclopropylamino-2-isopropylamino-5-pyrimidinecarbonitrile. The reaction product was recrystallized from methylcyclohexane to give 4-methoxy-6-(1-methylethylamino)-2-(2-methylpropylamino)-5-pyrimidinecarbonitrile; mp, 99°–101°.

Analysis: Calculated for $C_{13}H_{21}N_5O$: C,59.29; H,8.04; N,26.16; Found: C,59.15; H,7.68; N,25.79.

The ability of the herbicidally active compounds to control undesired plant growth was demonstrated as follows:

For preemergence tests, rows of the seeds of lima bean (*Phaseolus lunatus*), corn (*Zea mays*), wild oats (*Avena fatua*), lettuce (*Lactuca sativa*), mustard (*Brassica juncea*) and crabgrass (*Digitaria sanguinalis*) were planted together in 15 cm by 20 cm by 8 cm flats containing approximately 5 cm of sandy loam soil. After planting, an aqueous acetone solution of one of the active compounds was sprayed directly on the soil and exposed seeds, the active compound being applied uniformly at 8.96 kg per hectare. A thin layer of soil, approximately 1.3 cm deep, was then applied over the seeds. The flats were maintained in a greenhouse, and watered regularly on the surface of the soil for 10–14 days. At the end of this period, the phytotoxicity of the compound was recorded. Individual plant species were examined for percent kill, and a vigor rating of 0 to 5 was assigned to the surviving plants, a vigor rating of 5 signifying no chemical injury, 4- slight injury (plants have or are expected to recover), 3- moderate to severe injury (plants expected to recover in time), 2- moderate to severe injury (plants not expected to recover), 1- severe injury (plants not expected to recover), and 0- complete kill. Table 1 lists data collected in preemergence tests with herbicidally active compounds of the present invention.

TABLE I

| PREEMERGENCE HERBICIDAL ACTIVITY OF 5-PYRIMIDINECARBONITRILES* | | | | | | | | | | | |
|---|---|---|---|---|---|---|---|---|---|---|---|
| Active Compound | Lima Bean | | Corn | | Wild Oats | | Lettuce | | Mustard | | Crabgrass | |
| of Example | K | V | K | V | $K^a$ | | K | V | K | V | K | V |
| XXXIII | 0 | 3 | 0 | 3 | 0 | | 100 | 0 | 100 | 0 | 80 | 2 |
| XXXIV | 0 | 2 | 0 | 2 | 0 | | 100 | 0 | 100 | 0 | 100 | 0 |
| XXXV | 0 | 5 | 0 | 4 | 0 | | 0 | 4 | 30 | 4 | 0 | 4 |
| XXXVI | 0 | 4 | 0 | 3 | 0 | | 90 | 1 | 90 | 1 | 90 | 1 |
| XXXVII | 0 | 5 | 0 | 4 | 0 | | 60 | 4 | 100 | 0 | 90 | 1 |
| XXXVIII | 0 | 5 | 0 | 5 | 0 | | 0 | 5 | 0 | 4 | 90 | 1 |
| XXXIX | 0 | 5 | 0 | 5 | 0 | | 0 | 4 | 80 | 2 | 0 | 4 |
| XL | 0 | 5 | 0 | 5 | 0 | | 0 | 4 | 0 | 4 | 0 | 4 |
| XLI | 0 | 5 | 0 | 5 | 0 | | 100 | 0 | 100 | 0 | 100 | 0 |
| XLII | 0 | 5 | 0 | 5 | 0 | | 0 | 3 | 100 | 0 | 80 | 2 |
| XLIII | 0 | 5 | 0 | 5 | 0 | | 0 | 4 | 80 | 2 | 90 | 1 |
| XLIV | 0 | 4 | 0 | 5 | 0 | | 0 | 5 | 0 | 5 | 0 | 4 |
| XLV | 0 | 5 | 0 | 5 | 0 | | 80 | 3 | 100 | 0 | 100 | 0 |
| XLVII | 0 | 5 | 0 | 5 | 0 | | 0 | 4 | 90 | 1 | 0 | 4 |
| XLVIII | 0 | 5 | 0 | 5 | 0 | | 0 | 5 | 90 | 1 | 50 | 3 |
| XLIX | 100 | 0 | 0 | 2 | 0 | | 100 | 0 | 100 | 0 | 85 | 2 |
| LIII | 0 | 3 | 0 | 4 | 0 | | 0 | 2 | 80 | 2 | 0 | 3 |
| LVI | 0 | 4 | 0 | 4 | 0 | | 0 | 3 | 0 | 3 | 0 | 3 |
| LVII | 0 | 5 | 0 | 5 | 0 | | 0 | 4 | 40 | 4 | 0 | 4 |

*Entries under K refer to percent kill; under V, to plant vigor, a vigor of 5 signifying no chemical injury. 5-Pyrimidinecarbonitrile applied uniformily at 8.96 kg per hectare.
$^a$Surviving plants expected to recover.

In postemergence tests, untreated plants prepared as described above were maintained in a greenhouse and watered regularly for a period of 10 - 14 days, until the first trifoliate leaves of the bean plants were unfolding. The plants were then sprayed uniformly with an aqueous acetone solution of one of the herbicidally active compounds at 8.96 kg per hectare as in the preemergence tests. The treated plants were maintained in a greenhouse and watered regularly for an additional 10 - 14 days. At the end of that time the phytotoxicity of the compound was recorded as in the preemergence tests. The results of these tests appear in Table 2.

cluded in some instances, and various rates of application ranging downward from 8.96 kg per hectare were employed. The following plant species were added in some tests: sugarbeen (Beta vulgaris); onion (Allium cepa); green foxtain (Setaria viridis); soybean (Glycine max); cotton (Gossypium hirsutum); sorghum (Sorghum vulgare); sicklepod (Cassia obtusifolia); barley (Hordeum vulgare); barnyardgrass (Echinochloa crusgalli); peanut (Arachis hypogaea); safflower (Carthamus tinctorius); tomato (Lycopersicon esculentum); flax (Linum usitatissimum); rice (Oryza sativa); wheat (Triticum aestivum); cocklebur (Xanthium pensylvanicum); pigweed (Ama-

TABLE 2

| POSTEMERGENCE HERBICIDAL ACTIVITY OF 5-PYRIMIDINECARBONITRILES* | | | | | | | | | | | | |
|---|---|---|---|---|---|---|---|---|---|---|---|---|
| Active Compound | Lima Bean | | Corn | | Wild Oats | | Lettuce | | Mustard | | Crabgrass | |
| of Example | K | V | K | V | K | V | K | V | K | V | K | V |
| XXXIII | 0 | 4 | 0 | 5 | 0 | 4 | 100 | 0 | 100 | 0 | 0 | 5 |
| XXXIV | 100 | 0 | 0 | 5 | 0 | 5 | 100 | 0 | 100 | 0 | 100 | 0 |
| XXXV | 100 | 0 | 100 | 0 | 100 | 0 | 100 | 0 | 100 | 0 | 100 | 0 |
| XXXVI | 100 | 0 | 0 | 4 | 80 | 2 | 100 | 0 | 100 | 0 | 100 | 0 |
| XXXVII | 0 | 3 | 0 | 3 | 100 | 0 | 100 | 0 | 100 | 0 | 100 | 0 |
| XXXVIII | 0 | 3 | 75 | 3 | 100 | 0 | 100 | 0 | 90 | 1 | 90 | 1 |
| XXXIX | 0 | 4 | 0 | 3 | 90 | 1 | 100 | 0 | 100 | 0 | 100 | 0 |
| XL | 0 | 4 | 0 | 5 | 0 | 5 | 90 | 1 | 90 | 1 | 100 | 0 |
| XLI | 100 | 0 | 0 | 5 | 50 | 4 | 100 | 0 | 100 | 0 | 100 | 0 |
| XLII | 0 | 4 | 0 | 5 | 0 | 4 | 90 | 1 | 100 | 0 | 90 | 1 |
| XLIII | 0 | 4 | 75 | 1 | 0 | 4 | 80 | 2 | 100 | 0 | 85 | 2 |
| XLIV | 0 | 2 | 0 | 5 | 0 | 3 | 100 | 0 | 100 | 0 | 100 | 0 |
| XLV | 100 | 0 | 25 | 4 | 0 | 3 | 100 | 0 | 100 | 0 | 100 | 0 |
| XLVII | 50 | 3 | 0 | 5 | 0 | 5 | 100 | 0 | 100 | 0 | 100 | 0 |
| XLVIII | 0 | 5 | 0 | 5 | 0 | 5 | 100 | 0 | 100 | 0 | 100 | 0 |
| XLIX | 100 | 0 | 100 | 0 | 100 | 0 | 100 | 0 | 100 | 0 | 100 | 0 |
| LIII | 0 | 3 | 0 | 5 | 0 | 5 | 0 | 4 | 39 | 4 | 80 | 2 |
| LVI | 0 | 3 | 0 | 5 | 0 | 4 | 50 | 2 | 0 | 3 | 0 | 4 |
| LVII | 0 | 5 | 0 | 5 | 0 | 5 | 0 | 5 | 0 | 5 | 0 | 5 |

*Entries under K refer to percent kill; under V, to plant vigor, a vigor of 5 signifying no chemical injury. 5-Pyrimidinecarbonitrile applied uniformly at 8.96 kg per hectare.

The effect of the amount of active compound applied per hectare upon performance as a preemergence herbicide was determined for several 5-pyrimidinecarbonitriles. The evaluations were conducted as described above, except that additional plant species were included.

ranthus retroflexus); morningglory (Ipomoea purpurea); rape (Brassica campestris); prickly sida (Sida spinosa L.); lambsquarter (Chenopodium album). The results of these tests appear in Tables 3 through 21.

TABLE 3

| EFFECT OF APPLICATION LEVEL ON PREEMERGENCE PERFORMANCE OF 2-(1-CYANO-1-METHYL-ETHYLAMINO)-6-ETHYLAMINO-4-METHOXY-5-PYRIMIDINE PYRIMIDINECARBONITRILE (Example XXXIII)* | | | | | | | | | |
|---|---|---|---|---|---|---|---|---|---|
| | 0.14 kg/ha | 0.28 kg/ha | | 0.56 kg/ha | | 1.12 kg/ha | | 2.24 kg/ha | |
| Crop | $K^a$ | K | V | K | V | K | V | K | V |
| Lima Bean | 0 | 0 | 5 | 0 | 5 | 25 | 4 | 100 | 0 |
| Corn | 0 | 0 | 5 | 0 | 5 | 0 | 5 | 0 | 5 |
| Wild Oat | 0 | 0 | 5 | 0 | 5 | 20 | 4 | 20 | 4 |

TABLE 3-continued
EFFECT OF APPLICATION LEVEL ON PREEMERGENCE PERFORMANCE OF 2-(1-CYANO-1-METHYL-ETHYLAMINO)-6-ETHYLAMINO-4-METHOXY-5-PYRIMIDINE PYRIMIDINECARBONITRILE (Example XXXIII)*

| Crop | 0.14 kg/ha K[a] | 0.28 kg/ha K | V | 0.56 kg/ha K | V | 1.12 kg/ha K | V | 2.24 kg/ha K | V |
|---|---|---|---|---|---|---|---|---|---|
| Sugarbeet | 0 | 0 | 5 | 30 | 4 | 100 | 0 | 100 | 0 |
| Onion | 25 | 25 | 4 | 50 | 4 | 100 | 0 | 100 | 0 |
| Green Foxtail | 0 | 0 | 5 | 0 | 4 | 60 | 3 | 100 | 0 |
| Soybean | 0 | 0 | 5 | 0 | 5 | 0 | 4 | 75 | 3 |
| Cotton | 0 | 0 | 5 | 0 | 5 | 0 | 5 | 0 | 5 |
| Sorghum | 0 | 0 | 5 | 0 | 5 | 50 | 4 | 90 | 3 |
| Sicklepod | 0 | 0 | 5 | 0 | 5 | 0 | 5 | 0 | 4 |
| Barley | 0 | 0 | 5 | 0 | 5 | 10 | 4 | 75 | 4 |
| Barnyardgrass | 0 | 0 | 5 | 0 | 5 | 25 | 4 | 100 | 0 |
| Peanut | 0 | 0 | 5 | 0 | 5 | 0 | 5 | 0 | 5 |
| Safflower | 0 | 0 | 5 | 0 | 5 | 10 | 4 | 50 | 4 |
| Tomato | 0 | 0 | 5 | 0 | 5 | 80 | 4 | 100 | 0 |
| Flax | 0 | 0 | 5 | 50 | 4 | 90 | 2 | 100 | 0 |
| Rice | 0 | 0 | 5 | 0 | 5 | 0 | 5 | 100 | 0 |
| Wheat | 0 | 0 | 5 | 0 | 5 | 10 | 4 | 75 | 4 |
| Nutsedge | 0 | 0 | 5 | 0 | 5 | 0 | 5 | 0 | 5 |
| Lettuce | — | 20 | 4 | 80 | 3 | 100 | 0 | 100 | 0 |
| Mustard | — | 95 | 1 | 100 | 0 | 100 | 0 | 100 | 0 |
| Crabgrass | — | 90 | 1 | 90 | 1 | 100 | 0 | 100 | 0 |

*Entries under K refer to percent kill; under V, to plant vigor, a vigor of 5 signifying no chemical injury.
[a]Surviving plants expected to recover.

TABLE 4
EFFECT OF APPLICATION LEVEL ON PREEMERGENCE PERFORMANCE OF 2-(1-CYANO-1-METHYL-PROPYLAMINO)-6-ISOPROPYLAMINO-4-METHOXY-5-PYRIMIDINECARBONITRILE (Example XXXIV)*

| Crop | 0.28 kg/ha K[a] | 0.56 kg/ha K | V | 1.12 kg/ha K | V | 2.24 kg/ha K | V | 4.48 kg/ha K | V |
|---|---|---|---|---|---|---|---|---|---|
| Lima Bean | 0 | 0 | 5 | 0 | 4 | 0 | 4 | 50 | 2 |
| Corn | 0 | 0 | 5 | 0 | 5 | 0 | 5 | 0 | 5 |
| Wild Oats | 0 | 0 | 5 | 0 | 5 | 20 | 4 | 75 | 3 |
| Lettuce | 0 | 75 | 4 | 100 | 0 | 100 | 0 | 100 | 0 |
| Mustard | 0 | 75 | 2 | 90 | 1 | 100 | 0 | 100 | 0 |
| Crabgrass | 0 | 60 | 4 | 80 | 1 | 100 | 0 | 100 | 0 |

*Entries under K refer to percent kill; under V, to plant vigor, a vigor of 5 signifying no chemical injury.
[a]Surviving plants expected to recover.

TABLE 5
EFFECT OF APPLICATION LEVEL ON PREEMERGENCE PERFORMANCE OF 2-(1-CYANO-1-METHYLETHYLAMINO-6-ISOPROPYLAMINO-4-METHOXY-5-PYRIMIDINE-CARBONITRILE (EXAMPLE XXXV)*

| CROP | 0.28 kg/ha K[a] | 0.56 kg/ha K[a] | 1.12 kg/ha K | V | 2.24 kg/ha K | V |
|---|---|---|---|---|---|---|
| Lima Bean | 0 | 0 | 0 | 5 | 100 | 0 |
| Corn | 0 | 0 | 0 | 5 | 30 | 0 |
| Wild Oat | 0 | 0 | 0 | 5 | 0 | 5 |
| Sugarbeet | 0 | 10 | 100 | 0 | 100 | 0 |
| Onion | 30 | 75 | 100 | 0 | 100 | 0 |
| Green Foxtail | 0 | 0 | 50 | 4 | 100 | 0 |
| Soybean | 0 | 0 | 0 | 5 | 0 | 5 |
| Cotton | 0 | 0 | 0 | 5 | 0 | 5 |
| Sorghum | 0 | 0 | 0 | 5 | 0 | 5 |
| Sicklepod | 0 | 0 | 0 | 5 | 0 | 5 |
| Barley | 0 | 0 | 30 | 4 | 100 | 0 |
| Barnyardgrass | 0 | 0 | 10 | 4 | 100 | 0 |
| Peanut | 0 | 0 | 0 | 5 | 0 | 5 |
| Safflower | 0 | 0 | 0 | 5 | 0 | 4 |
| Tomato | 0 | 0 | 25 | 4 | 100 | 0 |
| Flax | 0 | 0 | 50 | 4 | 100 | 0 |
| Rice | 0 | 0 | 0 | 5 | 50 | 4 |
| Wheat | 0 | 0 | 10 | 4 | 75 | 3 |
| Nutsedge | 0 | 0 | 0 | 5 | 0 | 5 |

*Entries under K refer to percent kill; under V, to plant vigor, a vigor rating of 5 signifying no chemical injury.
[a]Surviving plants expected to recover.

TABLE 6
EFFECT OF APPLICATION LEVEL ON PREEMERGENCE PERFORMANCE OF 6-ETHYLAMINO-2-ISOPROPYLAMINO-4-METHOXY-5-PYRIMIDINECARBONITRILE (Example XXXVI)*

| CROP | 2.24 kg/ha K[a] | 4.48 kg/ha K[a] | 8.96 kg/ha K | V |
|---|---|---|---|---|
| Lima Bean | 0 | 0 | 0 | 5 |
| Corn | 0 | 0 | 0 | 4 |
| Wild Oats | 0 | 0 | 0 | 3 |
| Lettuce | 0 | 25 | 75 | 2 |
| Mustard | 0 | 40 | 90 | 1 |
| Crabgrass | 0 | 0 | 0 | 2 |
| Nutsedge | 0 | 0 | 0 | 5 |

*Entries under K refer to percent kill, under V to plant vigor, a vigor of 5 signifying no chemical injury.
[a]Surviving plants expected to recover.

TABLE 7
EFFECT OF APPLICATION LEVEL ON PREEMERGENCE PERFORMANCE OF 6-ETHYLAMINO-4-METHOXY-2-METHYLAMINO-5-PYRIMIDINECARBONITRILE Example XLII)*

| CROP | 2.24 kg/ha K[a] | 4.48 kg/ha K | V |
|---|---|---|---|
| Lima Bean | 50 | 100 | 0 |
| Corn | 0 | 0 | 5 |
| Wild Oats | 0 | 0 | 4 |
| Lettuce | 0 | 25 | 4 |
| Mustard | 0 | 90 | 1 |
| Crabgrass | 0 | 75 | 2 |
| Nutsedge | 0 | 0 | 5 |

*Entries under K refer to percent kill; under V to plant vigor, a vigor of 5 signifying no chemical injury.
[a]Surviving plants expected to recover.

TABLE 8

EFFECT OF APPLICATION LEVEL ON PREEMERGENCE PERFORMANCE OF 6-ISOPROPYLAMINO-4-METHOXY-2-METHYLAMINO-5-PYRIMIDINECARBONITRILE (Example XLIII)*

| CROP | 2.24 kg/ha K[a] | 4.48 kg/ha K | V | 8.96 kg/ha K | V |
|---|---|---|---|---|---|
| Lima Bean | 0 | 0 | 5 | 0 | 4 |
| Corn | 0 | 0 | 5 | 0 | 5 |
| Wild Oats | 0 | 0 | 5 | 0 | 5 |
| Lettuce | 0 | 30 | 4 | 10 | 4 |
| Mustard | 0 | 30 | 4 | 40 | 4 |
| Crabgrass | 0 | 75 | 2 | 75 | 2 |
| Nutsedge | 0 | 0 | 5 | 0 | 5 |

*Entries under K refer to percent kill; under V, to plant vigor, a vigor rating of 5 signifying no chemical injury.
[a]Surviving plants expected to recover.

TABLE 9

EFFECT OF APPLICATION LEVEL ON PREEMERGENCE PERFORMANCE OF 6-DIETHYLAMINO-2-ETHYLAMINO-4-METHOXY-5-PYRIMIDINECARBONITRILE (Example XLV)*

| CROP | 4.48 kg/ha K[a] | 8.96 kg/ha K | V |
|---|---|---|---|
| Lima Bean | 0 | 0 | 5 |
| Corn | 0 | 0 | 5 |
| Wild Oats | 0 | 0 | 5 |
| Lettuce | 0 | 10 | 4 |
| Mustard | 30 | 100 | 0 |
| Crabgrass | 0 | 90 | 1 |
| Nutsedge | 0 | 0 | 5 |

*Entries under K refer to percent kill; under V, to plant vigor, a vigor rating of 5 signifying no chemical injury.
[a]Surviving plants expected to recover.

TABLE 10

EFFECT OF APPLICATION LEVEL ON PREEMERGENCE PERFORMANCE OF 4-ETHOXY-6-DIETHYLAMINO-2-ISOPROPYLAMINO-5-PYRIMIDINECARBONITRILE (Example XLVI)*

| CROP | 2.24 kg/ha K[a] | 4.48 kg/ha K[a] |
|---|---|---|
| Lima Bean | 0 | 0 |
| Corn | 0 | 0 |
| Wild Oat | 0 | 0 |
| Lettuce | 0 | 0 |
| Mustard | 0 | 0 |
| Crabgrass | 0 | 0 |
| Soybean | 0 | 0 |
| Cotton | 0 | 0 |
| Flax | 0 | 0 |
| Peanut | 0 | 0 |
| Rice | 0 | 0 |
| Sugarbeet | 0 | 0 |
| Rape | 0 | 0 |
| Foxtail | 0 | 0 |
| Sorghum | 0 | 0 |
| Barnyardgrass | 0 | 0 |
| Onion | 20 | 75 |
| Safflower | 0 | 0 |
| Prickly Sida | 0 | 0 |
| Morningglory | 0 | 0 |
| Tomato | 0 | 0 |
| Nutsedge | 0 | 0 |

*Entries under K refer to percent kill; under V, to plant vigor, a vigor rating of 5 signifying no chemical injury.
[a]Surviving plants expected to recover.

TABLE 11

EFFECT OF APPLICATION LEVEL ON PREEMERGENCE PERFORMACE OF 2-(1-CYANO-1-METHYLETHYLAMINO)-4-METHOXY-6-(1-METHYLBUTYLAMINO)-5-PYRIMIDINE-CARBONITRILE (Example XLVII)*

| CROP | 0.28 kg/ha K[a] | 0.56 kg/ha K | V | 1.12 kg/ha K | V | 2.24 kg/ha K | V | 4.48 kg/ha K | V |
|---|---|---|---|---|---|---|---|---|---|
| Rice | 0 | 0 | 5 | 0 | 5 | 0 | 5 | 0 | 5 |
| Flax | 0 | 0 | 5 | 0 | 5 | 0 | 5 | 0 | 5 |
| Safflower | 0 | 0 | 5 | 0 | 5 | 0 | 5 | 0 | 5 |
| Tomato | 0 | 0 | 5 | 0 | 5 | 0 | 5 | 0 | 5 |
| Peanut | 0 | 0 | 5 | 0 | 5 | 0 | 5 | 0 | 5 |
| Wheat | 0 | 0 | 5 | 0 | 5 | 0 | 5 | 0 | 5 |
| Morningglory | 0 | 0 | 5 | 0 | 5 | 0 | 5 | 0 | 5 |
| Sugarbeet | 0 | 100 | 0 | 100 | 0 | 100 | 0 | 100 | 0 |
| Lima Bean | 0 | 0 | 5 | 0 | 5 | 0 | 5 | 0 | 5 |
| Corn | 0 | 0 | 5 | 0 | 5 | 0 | 5 | 0 | 4 |
| Soybean | 0 | 0 | 5 | 0 | 5 | 0 | 5 | 0 | 5 |
| Oat | 0 | 0 | 5 | 0 | 5 | 0 | 5 | 0 | 5 |
| Sorghum | 0 | 0 | 5 | 0 | 5 | 0 | 5 | 0 | 5 |
| Barley | 0 | 0 | 5 | 0 | 5 | 0 | 5 | 0 | 5 |
| Cotton | 0 | 0 | 5 | 0 | 5 | 0 | 5 | 0 | 5 |
| Sicklepod | 0 | 0 | 5 | 0 | 5 | 0 | 5 | 0 | 5 |
| Barnyardgrass | 0 | 0 | 5 | 0 | 5 | 0 | 5 | 0 | 4 |
| Foxtail | 0 | 0 | 5 | 0 | 5 | 0 | 5 | 0 | 4 |

*Entries under K refer to percent kill; under V, to plant vigor, a vigor rating of 5 signifying no chemical injury.
[a]Surviving plants expected to recover.

TABLE 12

EFFECT OF APPLICATION LEVEL ON PREEMERGENCE PERFORMANCE OF 2-(1-CYANO-1-METHYLETHYLAMINO)-6-CYCLOPROPYLAMINO-4-METHOXY-5-PYRIMIDINECARBONITRILE (Example XLIX)*

| CROP | 0.14 kg/ha K | V | 0.28 kg/ha K | V | 0.56 kg/ha K | V | 1.12 kg/ha K | V | 2.24 kg/ha K | V |
|---|---|---|---|---|---|---|---|---|---|---|
| Lima bean | 0 | 5 | 0 | 5 | 0 | 5 | 0 | 4 | 100 | 0 |
| Corn | 0 | 5 | 0 | 5 | 0 | 5 | 0 | 5 | 60 | 3 |
| Wild oat | 0 | 5 | 0 | 5 | 0 | 5 | 30 | 4 | 75 | 4 |
| Sugarbeet | 0 | 5 | 0 | 5 | 80 | 4 | 80 | 4 | 100 | 0 |
| Onion | 30 | 4 | 100 | 0 | 100 | 0 | 100 | 0 | 100 | 0 |
| Green Foxtail | 20 | 3 | 50 | 2 | 75 | 2 | 90 | 1 | 100 | 0 |
| Soybean | 0 | 5 | 0 | 5 | 0 | 5 | 0 | 4 | 75 | 0 |
| Cotton | 0 | 5 | 0 | 5 | 0 | 5 | 0 | 5 | 0 | 5 |
| Lettuce | — | — | — | — | 90 | 2 | 100 | 0 | 100 | 0 |
| Mustard | — | — | — | — | 90 | 2 | 100 | 0 | 100 | 0 |
| Crabgrass | — | — | — | — | 75 | 3 | 100 | 0 | 100 | 0 |
| Sorghum | 0 | 5 | 0 | 5 | 0 | 5 | 0 | 4 | 30 | 4 |

TABLE 12-continued
EFFECT OF APPLICATION LEVEL ON PREEMERGENCE PERFORMANCE OF 2-(1-CYANO-1-METHYLETHYLAMINO)-6-CYCLOPROPYLAMINO-4-METHOXY-5-PYRIMIDINECARBONITRILE (Example XLIX)*

| | 0.14 kg/ha | | 0.28 kg/ha | | 0.56 kg/ha | | 1.12 kg/ha | | 2.24 kg/ha | |
|---|---|---|---|---|---|---|---|---|---|---|
| CROP | K | V | K | V | K | V | K | V | K | V |
| Sicklepod | 0 | 5 | 0 | 5 | 0 | 5 | 0 | 4 | 0 | 4 |
| Barley | 0 | 5 | 0 | 5 | 0 | 5 | 0 | 5 | 0 | 4 |
| Barnyardgrass | 0 | 5 | 0 | 4 | 0 | 4 | 30 | 4 | 80 | 2 |
| Peanut | 0 | 5 | 0 | 5 | 0 | 5 | 0 | 5 | 0 | 5 |
| Safflower | 0 | 5 | 0 | 5 | 20 | 4 | 75 | 2 | 100 | 0 |
| Tomato | 0 | 5 | 0 | 4 | 75 | 3 | 75 | 3 | 100 | 0 |
| Flax | 0 | 5 | 0 | 5 | 75 | 4 | 75 | 3 | 100 | 0 |
| Rice | 0 | 5 | 0 | 5 | 0 | 5 | 40 | 4 | 100 | 0 |
| Wheat | 0 | 5 | 0 | 5 | 0 | 5 | 30 | 4 | 100 | 0 |
| Nutsedge | 0 | 5 | 0 | 5 | 0 | 5 | 0 | 5 | 0 | 5 |

*Entries under K refer to percent kill; under V, to plant vigor, a vigor rating of 5 signifying no chemical injury.

TABLE 13
EFFECT OF APPLICATION LEVEL ON PREEMERGENCE PERFORMANCE OF 6-AMINO-2-(1-CYANO-1-METHYLETHYLAMINO)-4-METHOXY-5-PYRIMIDINECARBONITRILE (Example L)*

| | 0.56 kg/ha | | 1.12 kg/ha | | 2.24 kg/ha | | 4.48 kg/ha | | 8.96 kg/ha | |
|---|---|---|---|---|---|---|---|---|---|---|
| CROP | K | V | K | V | K | V | K | V | K | V |
| Lima Bean | 0 | 4 | 100 | 0 | 100 | 0 | 100 | 0 | 100 | 0 |
| Corn | 0 | 5 | 60 | 4 | 100 | 0 | 100 | 0 | 100 | 0 |
| Wild Oat | 0 | 5 | 10 | 4 | 100 | 0 | 100 | 0 | 100 | 0 |
| Lettuce | 90 | 1 | 100 | 0 | 100 | 0 | 100 | 0 | 100 | 0 |
| Mustard | 0 | 4 | 60 | 4 | 100 | 0 | 100 | 0 | 100 | 0 |
| Crabgrass | 30 | 3 | 30 | 3 | 80 | 1 | 100 | 0 | 100 | 0 |
| Nutsedge | 0 | 5 | 0 | 5 | 0 | 5 | 0 | 5 | 0 | 4 |

*Entries under K refer to percent kill; under V, to plant vigor, a vigor rating of 5 signifying no chemical injury.

TABLE 14
EFFECT OF APPLICATION LEVEL ON PREEMERGENCE PERFORMANCE OF 6-BUTYLAMINO-2-(1-CYANO-1-METHYLETHYLAMINO)-4-METHOXY-5-PYRIMIDINECARBONITRILE (Ex. LI)*

| | 0.56 kg/ha | 1.12 kg/ha | 2.24 kg/ha | | 4.48 kg/ha | |
|---|---|---|---|---|---|---|
| CROP | K$^a$ | K$^a$ | K | V | K | V |
| Lima Bean | 0 | 0 | 0 | 5 | 0 | 4 |
| Corn | 0 | 0 | 0 | 5 | 0 | 5 |
| Wild Oats | 0 | 0 | 0 | 5 | 40 | 0 |
| Lettuce | 0 | 0 | 75 | 0 | 100 | 0 |
| Mustard | 0 | 40 | 100 | 0 | 100 | 0 |
| Crabgrass | 0 | 10 | 40 | 3 | 100 | 0 |
| Nutsedge | 0 | 0 | 0 | 5 | 0 | 5 |
| Morningglory | 0 | 0 | 0 | 5 | 0 | 4 |
| Peanut | 0 | 0 | 0 | 4 | 0 | 4 |
| Soybean | 0 | 0 | 0 | 5 | 0 | 5 |
| Sicklepod | 0 | 0 | 0 | 5 | 0 | 5 |
| Barley | 0 | 0 | 0 | 5 | 0 | 5 |
| Wheat | 0 | 0 | 0 | 5 | 0 | 4 |
| Flax | 0 | 0 | 30 | 4 | 30 | 4 |
| Safflower | 0 | 0 | 0 | 5 | 0 | 5 |
| Lambsquarter | 30 | 75 | 100 | 0 | 100 | 0 |
| Barnyardgrass | 0 | 0 | 0 | 5 | 0 | 5 |
| Green Foxtail | 0 | 0 | 100 | 0 | 100 | 0 |
| Tomato | 0 | 0 | 20 | 4 | 100 | 0 |

*Entries under K refer to percent kill; under V, to plant vigor, a vigor rating of 5 signifying no chemical injury.
$^a$Surviving plants expected to recover.

TABLE 15
EFFECT OF APPLICATION LEVEL ON PREEMERGENCE PERFORMANCE OF 2-(1-CYANO-1-METHYLPROPYLAMINO)-6-CYCLOPROPYLAMINO-4-METHOXY-5-PYRIMIDINECARBONITRILE (Example LII)*

| | 0.56 kg/ha | | 1.12 kg/ha | | 2.24 kg/ha | | 4.48 kg/ha | |
|---|---|---|---|---|---|---|---|---|
| CROP | K | V | K | V | K | V | K | V |
| Lima Bean | 0 | 5 | 0 | 5 | 100 | 0 | 100 | 0 |
| Corn | 0 | 5 | 0 | 5 | 0 | 4 | 60 | 0 |
| Wild Oats | 0 | 5 | 0 | 5 | 50 | 4 | 100 | 0 |
| Lettuce | 0 | 4 | 75 | 2 | 100 | 0 | 100 | 0 |
| Mustard | 100 | 0 | 100 | 0 | 100 | 0 | 100 | 0 |
| Crabgrass | 25 | 3 | 60 | 2 | 75 | 1 | 100 | 0 |
| Tomato | 0 | 4 | 100 | 0 | 100 | 0 | 100 | 0 |
| Wheat | 0 | 5 | 0 | 4 | 100 | 0 | 100 | 0 |
| Safflower | 0 | 5 | 0 | 5 | 20 | 4 | 100 | 0 |
| Peanut | 0 | 5 | 0 | 4 | 0 | 4 | 0 | 4 |
| Soybean | 0 | 5 | 0 | 5 | 0 | 4 | 80 | 2 |
| Cotton | 0 | 5 | 0 | 5 | 0 | 5 | 0 | 5 |
| Rice | 0 | 5 | 0 | 5 | 50 | 4 | 90 | 2 |
| Sorghum | 0 | 5 | 0 | 5 | 0 | 4 | 100 | 0 |
| Barnyardgrass | 0 | 5 | 0 | 3 | 100 | 0 | 100 | 0 |
| Sicklepod | 0 | 5 | 0 | 5 | 0 | 5 | 100 | 0 |
| Morningglory | 0 | 5 | 100 | 0 | 100 | 0 | 100 | 0 |

TABLE 15-continued
EFFECT OF APPLICATION LEVEL ON PREEMERGENCE PERFORMANCE OF 2-(1-CYANO-1-METHYLPROPYLAMINO)-6-CYCLOPROPYLAMINO-4-METHOXY-5-PYRIMIDINECARBONITRILE (Example LII)*

| CROP | 0.56 kg/ha | | 1.12 kg/ha | | 2.24 kg/ha | | 4.48 kg/ha | |
|---|---|---|---|---|---|---|---|---|
| | K | V | K | V | K | V | K | V |
| Nutsedge | 0 | 5 | 0 | 5 | 0 | 5 | 0 | 5 |

*Entries under K refer to percent kill; under V, to plant vigor, a vigor rating of 5 signifying no chemical injury.

TABLE 16
EFFECT OF APPLICATION LEVEL ON PREEMERGENCE PERFORMANCE OF 6-CYCLOPROPYLAMINO-2-ISOPROPYLAMINO-4-METHOXY-5-PYRIMIDINE-CARBONITRILE (Example LIV)*

| Crop | 0.14 kg/ha | | 0.28 kg/ha | | 0.56 kg/ha | | 1.12 kg/ha | | 2.24 kg/ha | |
|---|---|---|---|---|---|---|---|---|---|---|
| | K | V | K | V | K | V | K | V | K | V |
| Lima Bean | 0 | 5 | 0 | 5 | 0 | 5 | 0 | 4 | 75 | 2 |
| Corn | 0 | 5 | 0 | 5 | 0 | 5 | 0 | 5 | 0 | 4 |
| Wild Oat | 0 | 5 | 0 | 5 | 0 | 5 | 50 | 3 | 50 | 3 |
| Lettuce | 0 | 4 | 0 | 4 | 100 | 0 | 100 | 0 | 100 | 0 |
| Mustard | 0 | 4 | 0 | 4 | 75 | 4 | 90 | 2 | 100 | 0 |
| Crabgrass | 0 | 5 | 0 | 3 | 75 | 3 | 90 | 1 | 100 | 0 |
| Tomato | 0 | 5 | 0 | 5 | 50 | 3 | 100 | 0 | 100 | 0 |
| Safflower | 0 | 5 | 0 | 5 | 0 | 5 | 0 | 5 | 0 | 4 |
| Flax | 100 | 0 | 100 | 0 | 100 | 0 | 100 | 0 | 100 | 0 |
| Wheat | 0 | 5 | 0 | 4 | 0 | 4 | 75 | 3 | 100 | 0 |
| Peanut | 0 | 5 | 0 | 5 | 0 | 5 | 0 | 5 | — | — |
| Soybean | 0 | 5 | 0 | 5 | 0 | 5 | 0 | 4 | 80 | 2 |
| Cotton | 0 | 5 | 0 | 5 | 0 | 5 | 0 | 5 | 0 | 5 |
| Rice | 0 | 5 | 0 | 5 | 0 | 5 | 0 | 4 | 20 | 4 |
| Sorghum | 0 | 5 | 0 | 5 | 0 | 5 | 100 | 0 | 75 | 3 |
| Barnyardgrass | 0 | 5 | 0 | 5 | 80 | 2 | 100 | 0 | 100 | 0 |
| Sicklepod | 0 | 5 | 0 | 5 | 0 | 5 | 0 | 5 | 20 | 4 |
| Morningglory | 0 | 5 | 0 | 5 | 25 | 4 | 100 | 0 | 100 | 0 |
| Nutsedge | 0 | 5 | 0 | 5 | 0 | 5 | 0 | 5 | 0 | 5 |

*Entries under K refer to percent kill; under V, to plant vigor, a vigor rating of 5 signifying no chemical injury.

TABLE 17
EFFECT OF APPLICATION LEVEL ON PREEMERGENCE PERFORMANCE OF 6-CYCLOPROPYLAMINO-2-DIETHYLAMINO-4-METHOXY-5-PYRIMIDINE-CARBONITRILE (Example LV)*

| Crop | 1.12 kg/ha | 2.24 kg/ha | | 4.48 kg/ha | | 8.96 kg/ha | |
|---|---|---|---|---|---|---|---|
| | $K^a$ | K | V | K | V | K | V |
| Lima Bean | 0 | 0 | 5 | 0 | 5 | 0 | 4 |
| Corn | 0 | 0 | 5 | 0 | 5 | 0 | 5 |
| Wild Oats | 0 | 0 | 5 | 0 | 4 | 90 | 2 |
| Lettuce | 0 | 0 | 4 | 100 | 0 | 100 | 0 |
| Mustard | 0 | 0 | 4 | 90 | 1 | 100 | 0 |
| Crabgrass | 0 | 100 | 0 | 100 | 0 | 100 | 0 |
| Nutsedge | 0 | 0 | 5 | 0 | 5 | 0 | 5 |

*Entries under K refer to percent kill; under V, to plant vigor, a vigor rating of 5 signifying no chemical injury.
$^a$Surviving plants expected to recover.

TABLE 18
EFFECT OF APPLICATION LEVEL ON PREEMERGENCE PERFORMANCE OF 2-CYCLOPROPYLAMINO-6-ISOPROPYLAMINO-4-METHOXY-5-PYRIMIDINE-CARBONITRILE (Example LVIII)*

| Crop | 2.24 kg/ha | 4.48 kg/ha | | 8.96 kg/ha | |
|---|---|---|---|---|---|
| | $K^a$ | K | V | K | V |
| Lima Bean | 0 | 0 | 5 | 0 | 5 |
| Corn | 0 | 0 | 5 | 0 | 5 |
| Wild Oats | 0 | 0 | 5 | 0 | 5 |
| Lettuce | 0 | 75 | 2 | 75 | 2 |
| Mustard | 0 | 0 | 4 | 75 | 2 |
| Crabgrass | 0 | 100 | 0 | 100 | 0 |
| Nutsedge | 0 | 0 | 5 | 0 | 5 |

*Entries under K refer to percent kill; under V, to plant vigor, a vigor rating of 5 signifying no chemical injury.
$^a$Surviving plants expected to recover.

TABLE 19
EFFECT OF APPLICATION LEVEL ON PREEMERGENCE PERFORMANCE OF 2,6-BIS(CYCLOPROPYLAMINO)-4-METHOXY-5-PYRIMIDINECARBO-NITRILE (Example LIX)*

| Crop | 0.56 kg/ha | 1.12 kg/ha | | 2.24 kg/ha | | 4.48 kg/ha | |
|---|---|---|---|---|---|---|---|
| | $K^a$ | K | V | K | V | K | V |
| Lima Bean | 0 | 0 | 4 | 0 | 4 | 100 | 0 |
| Corn | 0 | 0 | 5 | 0 | 5 | 30 | 2 |
| Wild Oats | 0 | 25 | 4 | 25 | 4 | 100 | 0 |
| Lettuce | 0 | 100 | 0 | 100 | 0 | 100 | 0 |
| Mustard | 0 | 0 | 4 | 50 | 2 | 100 | 0 |

TABLE 19-continued
EFFECT OF APPLICATION LEVEL ON PREEMERGENCE PERFORMANCE OF 2,6-BIS(CYCLOPROPYLAMINO)-4-METHOXY-5-PYRIMIDINECARBONITRILE (Example LIX)*

| Crop | 0.56 kg/ha K[a] | 1.12 kg/ha K | V | 2.24 kg/ha K | V | 4.48 kg/ha K | V |
|---|---|---|---|---|---|---|---|
| Crabgrass | 0 | 100 | 0 | 100 | 0 | 100 | 0 |
| Nutsedge | 0 | 0 | 5 | 0 | 5 | 0 | 5 |

*Entries under K refer to percent kill; under V, to plant vigor, a vigor rating of 5 signifying no chemical injury.
[a]Surviving plants expected to recover.

TABLE 20
EFFECT OF APPLICATION LEVEL ON PREEMERGENCE PERFORMANCE OF 6-CYCLOPROPYLAMINO-4-METHOXY-2-(1-METHYLPROPYLAMINO)-5-PYRIMIDINECARBONITRILE (Example LX)*

| Crop | 0.56 kg/ha K[a] | 1.12 kg/ha K | V | 2.24 kg/ha K | V |
|---|---|---|---|---|---|
| Lima Bean | 0 | 0 | 5 | 0 | 4 |
| Corn | 0 | 0 | 5 | 0 | 5 |
| Wild Oats | 0 | 0 | 5 | 20 | 4 |
| Lettuce | 0 | 40 | 4 | 80 | 3 |
| Mustard | 0 | 100 | 0 | 95 | 2 |
| Crabgrass | 10 | 30 | 4 | 40 | 3 |
| Soybean | 0 | 0 | 5 | 0 | 5 |
| Sorghum | 0 | 0 | 5 | 0 | 5 |
| Sesbania | 0 | 0 | 5 | 60 | 4 |
| Sicklepod | 0 | 0 | 5 | 20 | 4 |
| Green Foxtail | 50 | 50 | 4 | 90 | 2 |
| Peanuts | 0 | 0 | 5 | 0 | 5 |
| Cotton | 0 | 0 | 5 | 0 | 5 |
| Barnyardgrass | 0 | 0 | 4 | 30 | 3 |
| Johnsongrass | 0 | 20 | 4 | 0 | 4 |
| Downeybrome | 10 | 10 | 4 | 20 | 4 |
| Morningglory | 0 | 0 | 5 | 0 | 5 |

*Entries under K refer to percent kill; under V, to plant vigor, a vigor rating of 5 signifying no chemical injury.
[a]Surviving plants expected to recover.

TABLE 21
EFFECT OF APPLICATION LEVEL ON PREEMERGENCE PERFORMANCE OF 4-METHOXY-6-(1-METHYLETHYLAMINO)-2-(2-METHYLPROPYLAMINO)-5-PYRIMIDINECARBONITRILE (Example LXI)*

| Crop | 0.56 kg/ha K[a] | 1.12 kg/ha K[a] | 2.24 kg/ha K[a] |
|---|---|---|---|
| Lima Bean | 0 | 0 | 0 |
| Corn | 0 | 0 | 0 |
| Wild Oats | 0 | 0 | 0 |
| Lettuce | 0 | 10 | 60 |
| Mustard | 0 | 0 | 50 |
| Crabgrass | 0 | 60 | 40 |
| Soybean | 0 | 0 | 0 |
| Sorghum | 0 | 0 | 0 |
| Sesbania | 0 | 0 | 50 |
| Sicklepod | 0 | 0 | 0 |
| Green Foxtail | 0 | 0 | 50 |
| Peanuts | 0 | 0 | 0 |
| Cotton | 0 | 0 | 0 |
| Barnyardgrass | 0 | 0 | 0 |
| Johnsongrass | 0 | 0 | 0 |
| Downeybrome | 0 | 0 | 0 |
| Morningglory | 0 | 0 | 0 |

*Entries under K refer to percent kill; under V, to plant vigor, a vigor rating of 5 signifying no chemical injury.
[a]Surviving plants expected to recover.

In the same way, the effect of the amount of active compound applied per hectare upon performance as a postemergence herbicide was determined for several of the herbicidal 5-pyrimidinecarbonitriles. The results appear in Tables 22 – 43.

TABLE 22
Effect Of Application Level On Postemergence Performance Of 2-(1-Cyano-1-Methylpropylamino)-6-Isopropylamino-4-Methoxy-5-Pyrimidinecarbonitrile (Example XXXIV)*

| Crop | 0.28 kg/ha K | V | 0.56 kg/ha K | V | 1.12 kg/ha K | V | 2.24 kg/ha K | V | 4.48 kg/ha K | V |
|---|---|---|---|---|---|---|---|---|---|---|
| Lima Bean | 0 | 5 | 0 | 4 | 50 | 4 | 100 | 0 | 100 | 0 |
| Corn | 0 | 5 | 0 | 5 | 0 | 5 | 0 | 5 | 0 | 4 |
| Wild Oats | 0 | 5 | 0 | 5 | 0 | 4 | 10 | 4 | 30 | 4 |
| Lettuce | 100 | 0 | 100 | 0 | 100 | 0 | 100 | 0 | 100 | 0 |
| Mustard | 60 | 2 | 100 | 0 | 100 | 0 | 100 | 0 | 100 | 0 |
| Crabgrass | 50 | 4 | 100 | 0 | 100 | 0 | 100 | 0 | 100 | 0 |

*Entries under K refer to percent kill; under V, to plant vigor, a vigor rating of 5 signifying no chemical injury.

TABLE 23

Effect Of Application Level On Postemergence Performance Of 2-(1-Cyano-1-Methylethylamino)-6-Isopropylamino-4-Methoxy-5-Pyrimidinecarbonitrile (Example XXXV)*

| Crop | 0.28 kg/ha K | V | 0.56 kg/ha K | V | 1.12 kg/ha K | V | 2.24 kg/ha K | V |
|---|---|---|---|---|---|---|---|---|
| Lima Bean | 0 | 4 | 0 | 4 | 25 | 4 | 100 | 0 |
| Corn | 0 | 5 | 0 | 5 | 30 | 4 | 60 | 3 |
| Wild Oat | 0 | 5 | 0 | 5 | 0 | 5 | 50 | 4 |
| Sugarbeet | 50 | 4 | 100 | 0 | 100 | 0 | 100 | 0 |
| Onion | 80 | 2 | 100 | 0 | 100 | 0 | 100 | 0 |
| Green Foxtail | 75 | 4 | 100 | 0 | 100 | 0 | 100 | 0 |
| Soybean | 0 | 5 | 0 | 4 | 50 | 4 | 100 | 0 |
| Cotton | 0 | 5 | 0 | 5 | 0 | 5 | 0 | 5 |
| Sorghum | 0 | 5 | 0 | 5 | 0 | 4 | 0 | 4 |
| Sicklepod | 0 | 4 | 0 | 4 | 0 | 4 | 50 | 4 |
| Barley | 0 | 5 | 0 | 5 | 0 | 4 | 100 | 0 |
| Barnyardgrass | 20 | 4 | 20 | 4 | 80 | 2 | 100 | 0 |
| Peanut | 0 | 5 | 0 | 5 | 0 | 5 | 0 | 4 |
| Safflower | 100 | 0 | 100 | 0 | 100 | 0 | 100 | 0 |
| Tomato | 100 | 0 | 100 | 0 | 100 | 0 | 100 | 0 |
| Flax | 0 | 4 | 80 | 3 | 100 | 0 | 100 | 0 |
| Rice | 0 | 5 | 80 | 4 | 90 | 2 | 100 | 0 |
| Wheat | 0 | 5 | 0 | 4 | 30 | 4 | 100 | 0 |
| Nutsedge | 0 | 5 | 0 | 5 | 0 | 5 | 0 | 5 |
| Lettuce | — | — | 100 | 0 | 100 | 0 | — | — |
| Mustard | — | — | 100 | 0 | 100 | 0 | — | — |
| Crabgrass | — | — | 100 | 0 | 100 | 0 | — | — |

*Entries under K refer to percent kill; under V, to plant vigor, a vigor rating of 5 signifying no chemical injury.

TABLE 24

Effect Of Application Level On Postemergence Performance Of 2-(1-Cyano-1-Methylethylamino)-6-Ethylamino-4-Methoxy-5-Pyrimidinecarbonitrile (Example XXXIII)*

| CROP | 0.14 kg/ha K | V | 0.28 kg/ha K | V | 0.56 kg/ha K | V | 1.12 kg/ha K | V | 2.24 kg/ha K | V |
|---|---|---|---|---|---|---|---|---|---|---|
| Lima Bean | 0 | 5 | 0 | 5 | 0 | 5 | 75 | 4 | 100 | 0 |
| Corn | 0 | 5 | 0 | 5 | 0 | 5 | 0 | 4 | 100 | 0 |
| Wild Oats | 0 | 5 | 0 | 5 | 0 | 5 | 50 | 4 | 100 | 0 |
| Sugarbeet | 75 | 3 | 100 | 0 | 100 | 0 | 100 | 0 | 100 | 0 |
| Onion | 100 | 0 | 100 | 0 | 100 | 0 | 100 | 0 | 100 | 0 |
| Green Foxtail | 100 | 0 | 100 | 0 | 100 | 0 | 100 | 0 | 100 | 0 |
| Soybean | 0 | 4 | 0 | 4 | 20 | 4 | 90 | 2 | 100 | 0 |
| Cotton | 0 | 5 | 0 | 5 | 0 | 5 | 0 | 5 | 0 | 4 |
| Sorghum | 0 | 5 | 0 | 5 | 0 | 5 | 0 | 5 | 0 | 4 |
| Sicklepod | 0 | 4 | 0 | 4 | 50 | 4 | 75 | 4 | 100 | 0 |
| Barley | 0 | 4 | 0 | 4 | 10 | 4 | 100 | 0 | 100 | 0 |
| Barnyardgrass | 0 | 5 | 30 | 4 | 50 | 4 | 100 | 0 | 100 | 0 |
| Peanut | 0 | 5 | 0 | 5 | 0 | 5 | 100 | 0 | 100 | 0 |
| Safflower | 60 | 4 | 75 | 3 | 100 | 0 | 100 | 0 | 100 | 0 |
| Tomato | 75 | 4 | 100 | 0 | 100 | 0 | 100 | 0 | 100 | 0 |
| Flax | 0 | 4 | 100 | 0 | 100 | 0 | 100 | 0 | 100 | 0 |
| Rice | 10 | 4 | 20 | 4 | 80 | 2 | 100 | 0 | 100 | 0 |
| Wheat | 0 | 5 | 0 | 5 | 0 | 5 | 75 | 4 | 100 | 0 |
| Nutsedge | 0 | 5 | 0 | 5 | 0 | 5 | 0 | 5 | 0 | 5 |
| Lettuce | — | — | 100 | 0 | 100 | 0 | 100 | 0 | 100 | 0 |
| Mustard | — | — | 100 | 0 | 100 | 0 | 100 | 0 | 100 | 0 |
| Crabgrass | — | — | 80 | 4 | 100 | 0 | 100 | 0 | 100 | 0 |

*Entries under K refer to percent kill; under V, to plant vigor, a vigor rating of 5 signifying no chemical injury.

TABLE 25

Effect Of Application Level On Postemergence Performance Of 6-Ethylamino-2-Isopropylamino-4-Methoxy-5-Pyrimidinecarbonitrile (Example XXXVI)*

| CROP | 0.56 kg/ha K | V | 1.12 kg/ha K | V | 2.24 kg/ha K | V | 4.48 kg/ha K | V | 8.96 kg/ha K | V |
|---|---|---|---|---|---|---|---|---|---|---|
| Lima Beans | 0 | 4 | 0 | 4 | 0 | 4 | 0 | 4 | 0 | 3 |
| Corn | 0 | 5 | 0 | 5 | 0 | 5 | 0 | 5 | 0 | 5 |
| Wild Oats | 50 | 3 | 50 | 3 | 100 | 0 | 100 | 0 | 100 | 0 |
| Lettuce | 100 | 0 | 100 | 0 | 100 | 0 | 100 | 0 | 100 | 0 |
| Mustard | 100 | 0 | 100 | 0 | 100 | 0 | 100 | 0 | 100 | 0 |
| Crabgrass | 50 | 3 | 50 | 4 | 90 | 3 | 100 | 0 | 100 | 0 |
| Nutsedge | 0 | 5 | 0 | 5 | 0 | 5 | 0 | 5 | 0 | 5 |

*Entries under K refer to percent kill; under V, to plant vigor, a vigor rating of 5 signifying no chemical injury.

TABLE 26

Effect Of Application Level On Postemergence Performance Of 6-Diethylamino-2-Isopropylamino-4-Methoxy-5-Pyrimidinecarbonitrile (Example XXXIX)*

| Crop | 0.56 kg/ha K | V | 1.12 kg/ha K | V | 2.24 kg/ha K | V | 4.48 kg/ha K | V |
|---|---|---|---|---|---|---|---|---|
| Lima Beans | 0 | 4 | 0 | 4 | 0 | 4 | 0 | 4 |
| Corn | 0 | 4 | 0 | 4 | 0 | 4 | 0 | 4 |
| Wild Oats | 95 | 1 | 100 | 0 | 100 | 0 | 100 | 0 |
| Lettuce | 100 | 0 | 100 | 0 | 100 | 0 | 100 | 0 |
| Mustard | 100 | 0 | 100 | 0 | 100 | 0 | 100 | 0 |
| Crabgrass | 100 | 0 | 100 | 0 | 100 | 0 | 100 | 0 |
| Nutsedge | 0 | 5 | 0 | 5 | 0 | 5 | 0 | 5 |

*Entries under K refer to percent kill; under V, to plant vigor, a vigor rating of 5 signifying no chemical injury.

TABLE 27
Effect Of Application Level On Postemergence Performance Of 2-Ethylamino-6-Isopropylamino-4-Methoxy-5-Pyrimidine-Carbonitrile (Example XL)*

| Crop | 0.56 kg/ha K | V | 1.12 kg/ha K | V | 2.24 kg/ha K | V | 4.48 kg/ha K | V | 8.96 kg/ha K | V |
|---|---|---|---|---|---|---|---|---|---|---|
| Lima Beans | 0 | 5 | 0 | 5 | 0 | 5 | 0 | 5 | 0 | 4 |
| Corn | 0 | 5 | 0 | 5 | 0 | 5 | 0 | 5 | 0 | 5 |
| Wild Oats | 0 | 5 | 0 | 5 | 0 | 5 | 0 | 5 | 0 | 4 |
| Lettuce | 100 | 0 | 100 | 0 | 100 | 0 | 100 | 0 | 100 | 0 |
| Mustard | 0 | 5 | 0 | 5 | 0 | 5 | 0 | 5 | 0 | 5 |
| Crabgrass | 0 | 5 | 0 | 5 | 0 | 5 | 0 | 5 | 0 | 5 |
| Nutsedge | 0 | 5 | 0 | 5 | 0 | 5 | 0 | 5 | 0 | 5 |

*Entries under K refer to percent kill; under V, to plant vigor, a vigor rating of 5 signifying no chemical injury.

TABLE 28
Effect Of Application Level On Postemergence Performance Of 6-Ethylamino-4-Methoxy-2-Methylamino-5-Pyrimidinecarbonitrile (Examples XLII)*

| Crop | 1.12 kg/ha K[a] | 2.24 kg/ha K[a] | 4.48 kg/ha K | V |
|---|---|---|---|---|
| Lima Beans | 0 | 0 | 0 | 4 |
| Corn | 0 | 0 | 0 | 5 |
| Wild Oats | 0 | 0 | 0 | 4 |
| Lettuce | 0 | 60 | 100 | 0 |
| Mustard | 0 | 20 | 40 | 3 |
| Crabgrass | 0 | 0 | 20 | 4 |
| Nutsedge | 0 | 0 | 0 | 5 |

*Entries under K refer to percent kill; under V, to plant vigor, a vigor rating of 5 signifying no chemical injury.
[a]Surviving plants expected to recover.

TABLE 29
Effect Of Application Level On Postemergence Performance Of 6-Isopropylamino-4-Methoxy-2-Methylamino-5-Pyrimidinecarbonitrile (Example XLIII)*

| Crop | 2.24 kg/ha K[a] | 4.48 kg/ha K | V | 8.96 kg/ha K | V |
|---|---|---|---|---|---|
| Lima Beans | 0 | 0 | 4 | 0 | 4 |
| Corn | 0 | 0 | 5 | 0 | 5 |
| Wild Oats | 0 | 0 | 5 | 0 | 5 |
| Lettuce | 0 | 100 | 0 | 100 | 0 |
| Mustard | 0 | 100 | 0 | 100 | 0 |
| Crabgrass | 0 | 0 | 5 | 0 | 5 |
| Nutsedge | 0 | 0 | 5 | 0 | 5 |

*Entries under K refer to percent kill; under V, to plant vigor, a vigor rating of 5 signifying no chemical injury.
[a]Surviving plants expected to recover.

TABLE 30
Effect Of Application Level On Postemergence Performance Of 6-Diethylamino-2-Ethylamino-4-Methoxy-5-Pyrimidinecarbonitrile (Example XLV)*

| Crop | 1.12 kg/ha K[a] | 2.24 kg/ha K[a] | 4.48 kg/ha K | V | 8.96 kg/ha K | V |
|---|---|---|---|---|---|---|
| Lima Beans | 0 | 0 | 0 | 4 | 0 | 4 |
| Corn | 0 | 0 | 0 | 5 | 0 | 5 |
| Wild Oats | 0 | 0 | 0 | 5 | 10 | 4 |
| Lettuce | 0 | 60 | 100 | 0 | 100 | 0 |
| Mustard | 0 | 30 | 80 | 2 | 90 | 1 |
| Crabgrass | 0 | 20 | 75 | 2 | 80 | 2 |
| Nutsedge | 0 | 0 | 0 | 5 | 0 | 5 |

*Entries under K refer to percent kill; under V, to plant vigor, a vigor of 5 signifying no chemical injury.
[a]Surviving plants expected to recover.

TABLE 31
Effect Of Application Level On Postemergence Performance Of 4-Ethoxy-6-Diethylamino-2-Isopropylamino-5-Pyrimidinecarbonitrile (Example XLVI)*

| CROP | 0.28 kg/ha K | V | 0.56 kg/ha K | V | 1.12 kg/ha K | V | 2.24 kg/ha K | V | 4.48 kg/ha K | V |
|---|---|---|---|---|---|---|---|---|---|---|
| Lima Bean | 0 | 5 | 0 | 5 | 0 | 5 | 0 | 5 | 0 | 4 |
| Corn | 0 | 5 | 0 | 5 | 0 | 5 | 0 | 5 | 0 | 5 |
| Wild Oats | 0 | 5 | 0 | 5 | 0 | 5 | 0 | 5 | 0 | 4 |
| Lettuce | 100 | 0 | 100 | 0 | 100 | 0 | 100 | 0 | 100 | 0 |
| Mustard | 0 | 5 | 10 | 4 | 10 | 4 | 75 | 2 | 100 | 0 |
| Crabgrass | 0 | 5 | 0 | 4 | 60 | 2 | 85 | 1 | 100 | 0 |
| Soybean | 0 | 5 | 0 | 5 | 0 | 5 | 0 | 5 | 0 | 5 |
| Cotton | 0 | 5 | 0 | 5 | 0 | 5 | 0 | 5 | 0 | 5 |
| Flax | 0 | 5 | 0 | 4 | 20 | 4 | 100 | 0 | 100 | 0 |
| Peanut | 0 | 5 | 0 | 5 | 0 | 5 | 0 | 5 | 0 | 5 |
| Rice | 0 | 5 | 0 | 5 | 0 | 5 | 0 | 4 | 10 | 4 |
| Sugarbeet | — | — | — | — | 0 | 4 | 20 | 3 | 0 | 3 |
| Rape | 0 | 5 | 0 | 5 | 0 | 5 | 0 | 5 | 0 | 5 |
| Sorghum | 0 | 5 | 0 | 5 | 0 | 5 | 0 | 5 | 0 | 5 |
| Barnyardgrass | 0 | 5 | 0 | 5 | 0 | 5 | 0 | 5 | 0 | 5 |
| Onion | 0 | 4 | 0 | 4 | 10 | 3 | 100 | 0 | 100 | 0 |
| Safflower | 0 | 5 | 0 | 5 | 0 | 5 | 0 | 5 | 0 | 5 |
| Prickly Sida | 0 | 5 | 0 | 5 | 0 | 5 | 0 | 4 | 0 | 4 |
| Morningglory | 0 | 5 | 0 | 5 | 0 | 5 | 20 | 4 | 90 | 2 |
| Tomato | 0 | 5 | 0 | 4 | 20 | 4 | 80 | 3 | 100 | 0 |
| Nutsedge | 0 | 5 | 0 | 5 | 0 | 5 | 0 | 5 | 0 | 5 |

*Entries under K refer to percent kill; under V to plant vigor, a vigor of 5 signifying no chemical injury.

TABLE 32

Effect Of Application Level On Postemergence Performance Of 2-(1-Cyano-1-Methylamino)-4-Methoxy-6-(1-Methylbutylamino)-Pyrimidinecarbonitrile (Example XLVII)*

| CROP | 0.28 kg/ha | | 0.56 kg/ha | | 1.12 kg/ha | | 2.24 kg/ha | | 4.48 kg/ha | |
|---|---|---|---|---|---|---|---|---|---|---|
| | K | V | K | V | K | V | K | V | K | V |
| Rice | 0 | 5 | 0 | 5 | 0 | 5 | 0 | 5 | 0 | 5 |
| Flax | 100 | 0 | 100 | 0 | 100 | 0 | 100 | 0 | 100 | 0 |
| Safflower | 0 | 5 | 30 | 4 | 100 | 0 | 100 | 0 | 100 | 0 |
| Tomato | 0 | 5 | 0 | 5 | 0 | 4 | 100 | 0 | 100 | 0 |
| Peanut | 0 | 5 | 0 | 5 | 0 | 5 | 0 | 5 | 0 | 5 |
| Wheat | 0 | 5 | 0 | 5 | 0 | 5 | 0 | 5 | 0 | 5 |
| Morningglory | 0 | 5 | 0 | 5 | 0 | 5 | 0 | 5 | 0 | 4 |
| Sugarbeet | 100 | 0 | 100 | 0 | 100 | 0 | 100 | 0 | 100 | 0 |
| Lima Bean | 0 | 5 | 0 | 5 | 0 | 5 | 30 | 4 | 60 | 4 |
| Corn | 0 | 5 | 0 | 5 | 0 | 5 | 0 | 5 | 0 | 5 |
| Soybean | 0 | 5 | 0 | 5 | 0 | 5 | 0 | 5 | 0 | 5 |
| Oats | 0 | 5 | 0 | 5 | 0 | 5 | 0 | 5 | 0 | 5 |
| Sorghum | 0 | 5 | 0 | 5 | 0 | 5 | 0 | 5 | 0 | 5 |
| Barley | 0 | 5 | 0 | 5 | 0 | 5 | 0 | 4 | 0 | 4 |
| Cotton | 0 | 5 | 0 | 5 | 0 | 5 | 0 | 4 | 0 | 4 |
| Sicklepod | 0 | 5 | 0 | 5 | 0 | 5 | 0 | 5 | 0 | 5 |
| Barnyardgrass | 0 | 5 | 0 | 5 | 0 | 5 | 0 | 5 | 0 | 5 |
| Foxtail | 0 | 4 | 0 | 4 | 0 | 4 | 0 | 4 | 100 | 0 |

*Entries under K refer to percent kill; under V to plant vigor, a vigor of 5 signifying no chemical injury.

TABLE 33

EFFECT OF APPLICATION LEVEL ON POSTEMERGENCE PERFORMANCE OF 2-(1-CYANO-1-METHYLETHYLAMINO)-6-(1-ISOPROPYL-2-METHYLPROPYLAMINO)-4-METHOXY-5-PYRIMIDINECARBONITRILE (Example XLVIII)*

| Crop | 4.48 kg/ha K$^a$ | 8.96 kg/ha K$^a$ |
|---|---|---|
| Lima Bean | 0 | 0 |
| Corn | 0 | 0 |
| Wild Oat | 0 | 0 |
| Lettuce | 0 | 60 |
| Mustard | 0 | 0 |
| Crabgrass | 0 | 0 |
| Nutsedge | 0 | 0 |

*Entries under K refer to percent kill; under V to plant vigor, a vigor of 5 signifying no chemical injury.
$^a$Surviving plants expected to recover.

TABLE 34

2-(1-CYANO-1-METHYLETHYLAMINO)-6-CYCLOPROPYLAMINO-4-METHOXY-5-PYRIMIDINECARBONITRILE (Example XLIX)*

| Crop | 0.14 kg/ha | | 0.28 kg/ha | | 0.56 kg/ha | | 1.12 kg/ha | | 2.24 kg/ha | |
|---|---|---|---|---|---|---|---|---|---|---|
| | K | V | K | V | K | V | K | V | K | V |
| Lima Bean | 0 | 5 | 0 | 4 | 80 | 2 | 100 | 0 | 100 | 0 |
| Corn | 0 | 5 | 0 | 5 | 0 | 4 | 100 | 0 | 100 | 0 |
| Wild Oat | 0 | 5 | 0 | 5 | 0 | 5 | 0 | 4 | 100 | 0 |
| Sugarbeet | 100 | 0 | 100 | 0 | 100 | 0 | 100 | 0 | 100 | 0 |
| Onion | 100 | 0 | 100 | 0 | 100 | 0 | 100 | 0 | 100 | 0 |
| Green Foxtail | 100 | 0 | 100 | 0 | 100 | 0 | 100 | 0 | 100 | 0 |
| Soybean | 0 | 5 | 0 | 5 | 0 | 4 | 100 | 0 | 100 | 0 |
| Cotton | 0 | 5 | 0 | 5 | 10 | 4 | 100 | 0 | 100 | 0 |
| Sorghum | 0 | 5 | 0 | 5 | 0 | 5 | 75 | 4 | 100 | 0 |
| Sicklepod | 0 | 4 | 30 | 4 | 50 | 4 | 100 | 0 | 100 | 0 |
| Barnyardgrass | 0 | 5 | 0 | 5 | 100 | 0 | 100 | 0 | 100 | 0 |
| Peanut | 0 | 5 | 0 | 5 | 0 | 4 | 100 | 0 | 80 | 2 |
| Safflower | 80 | 4 | 100 | 0 | 100 | 0 | 100 | 0 | 100 | 0 |
| Tomato | 100 | 0 | 100 | 0 | 100 | 0 | 100 | 0 | 100 | 0 |
| Flax | 75 | 4 | 100 | 0 | 100 | 0 | 100 | 0 | 100 | 0 |
| Rice | 10 | 4 | 100 | 0 | 100 | 0 | 100 | 0 | 100 | 0 |
| Wheat | 0 | 5 | 10 | 4 | 75 | 4 | 100 | 0 | 100 | 0 |
| Nutsedge | 0 | 5 | 0 | 5 | 0 | 4 | 0 | 4 | 0 | 4 |
| Lettuce | — | — | — | — | 100 | 0 | 100 | 0 | 100 | 0 |
| Mustard | — | — | — | — | 100 | 0 | 100 | 0 | 100 | 0 |
| Crabgrass | — | — | — | — | 100 | 0 | 100 | 0 | 100 | 0 |

*Entries under K refer to percent kill; under V, to plant vigor, a vigor rating of 5 signifying no chemical injury.

TABLE 35

EFFECT OF APPLICATION LEVEL ON POSTEMERGENCE PERFORMANCE OF 6-AMINO-2-(1-CYANO-1-METHYLETHYLAMINO)-4-METHOXY-5-PYRIMIDINECARBONITRILE (Example L)*

| Crop | 0.56 kg/ha | | 1.12 kg/ha | | 2.24 kg/ha | | 4.48 kg/ha | | 8.96 kg/ha |
|---|---|---|---|---|---|---|---|---|---|
| | K | V | K | V | K | V | K | V | K |
| Lima Bean | 30 | 4 | 75 | 3 | 100 | 0 | 100 | 0 | 100 |
| Corn | 0 | 5 | 0 | 5 | 0 | 4 | 0 | 4 | 100 |
| Wild Oat | 0 | 5 | 10 | 4 | 50 | 3 | 100 | 0 | 100 |
| Lettuce | 100 | 0 | 100 | 0 | 100 | 0 | 100 | 0 | 100 |
| Mustard | 20 | 4 | 100 | 0 | 100 | 0 | 100 | 0 | 100 |
| Crabgrass | 0 | 5 | 0 | 5 | 0 | 4 | 100 | 0 | 100 |
| Nutsedge | 0 | 5 | 0 | 5 | 0 | 4 | 0 | 4 | 100 |

*Entries under K refer to percent kill; under V, to plant vigor, a vigor of 5 signifying no chemical injury.

TABLE 36

EFFECT OF APPLICATION LEVEL ON POSTEMERGENCE PERFORMANCE OF 6-BUTYLAMINO-2-(1-METHYLETHYLAMINO)-4-METHOXY-5-PYRIMIDINECARBONITRILE (Example LI)*

| Crop | 0.28 kg/ha | | 0.56 kg/ha | | 1.12 kg/ha | | 2.24 kg/ha | | 4.48 kg/ha | |
|---|---|---|---|---|---|---|---|---|---|---|
| | K | V | K | V | K | V | K | V | K | V |
| Lima Bean | 0 | 4 | 0 | 4 | 50 | 3 | 100 | 0 | 100 | 0 |
| Corn | 0 | 5 | 0 | 5 | 0 | 5 | 0 | 5 | 0 | 5 |
| Wild Oat | 0 | 5 | 0 | 5 | 0 | 5 | 0 | 5 | 0 | 5 |
| Lettuce | 100 | 0 | 100 | 0 | 100 | 0 | 100 | 0 | 100 | 0 |
| Mustard | 0 | 5 | 0 | 4 | 75 | 3 | 100 | 0 | 100 | 0 |
| Crabgrass | 0 | 5 | 0 | 5 | 0 | 5 | 90 | 2 | 100 | 0 |
| Nutsedge | 0 | 5 | 0 | 5 | 0 | 5 | 0 | 5 | 0 | 5 |
| Morningglory | 0 | 5 | 0 | 4 | 20 | 4 | 100 | 0 | 100 | 0 |
| Peanut | 0 | 5 | 0 | 5 | 0 | 5 | 0 | 5 | 0 | 5 |
| Soybean | 0 | 5 | 0 | 5 | 0 | 5 | 0 | 5 | 60 | 2 |
| Sicklepod | 0 | 5 | 0 | 5 | 0 | 5 | 0 | 4 | 60 | 4 |
| Barley | 0 | 5 | 0 | 5 | 0 | 5 | 0 | 4 | 0 | 4 |
| Wheat | 0 | 5 | 0 | 5 | 0 | 5 | 0 | 5 | 0 | 4 |
| Flax | 0 | 5 | 0 | 5 | 75 | 4 | 100 | 0 | 100 | 0 |
| Safflower | 0 | 5 | 0 | 5 | 0 | 5 | 0 | 5 | 0 | 5 |
| Lambsquarter | 90 | 2 | 90 | 2 | 100 | 0 | 100 | 0 | 100 | 0 |
| Barnyardgrass | 0 | 5 | 0 | 5 | 0 | 5 | 0 | 5 | 0 | 5 |
| Green Foxtail | 0 | 4 | 30 | 4 | 100 | 0 | 100 | 0 | 100 | 0 |
| Tomato | 60 | 4 | 60 | 4 | 100 | 0 | 100 | 0 | 100 | 0 |

*Entries under K refer to percent kill; under V, to plant vigor, a vigor of 5 signifying no chemical injury.

TABLE 37
EFFECT OF APPLICATION LEVEL ON POSTEMERGENCE PERFORMANCE OF 2-(1-CYANO-1-METHYLPROPYLAMINO)-6-CYCLOPROPYLAMINO-4-METHOXY-5-PYRIMIDINECARBONITRILE
(Example LII)*

| Crop | 0.56 kg/ha K | V | 1.12 kg/ha K | V | 2.24 kg/ha K | V | 4.48 kg/ha K | V |
|---|---|---|---|---|---|---|---|---|
| Lima Bean | 0 | 4 | 75 | 3 | 100 | 0 | 100 | 0 |
| Corn | 0 | 5 | 0 | 5 | 0 | 5 | 0 | 5 |
| Wild Oat | 0 | 5 | 0 | 5 | 0 | 5 | 50 | 4 |
| Lettuce | 100 | 0 | 100 | 0 | 100 | 0 | 100 | 0 |
| Mustard | 100 | 0 | 100 | 0 | 100 | 0 | 100 | 0 |
| Crabgrass | 100 | 0 | 100 | 0 | 100 | 0 | 100 | 0 |
| Tomato | 100 | 0 | 100 | 0 | 100 | 0 | 100 | 0 |
| Flax | 90 | 1 | 100 | 0 | 100 | 0 | 100 | 0 |
| Wheat | 0 | 5 | 0 | 5 | 20 | 4 | 100 | 0 |
| Safflower | 100 | 0 | 100 | 0 | 100 | 0 | 100 | 0 |
| Peanut | 0 | 5 | 0 | 5 | 0 | 5 | 0 | 5 |
| Soybean | 0 | 5 | 20 | 4 | 100 | 0 | 100 | 0 |
| Cotton | 0 | 4 | 25 | 4 | 100 | 0 | 100 | 0 |
| Rice | 0 | 5 | 0 | 5 | 100 | 0 | 100 | 0 |
| Sorghum | 0 | 5 | 0 | 5 | 100 | 0 | 100 | 0 |
| Sicklepod | 20 | 4 | 20 | 4 | 75 | 4 | 90 | 2 |
| Barnyardgrass | 40 | 3 | 100 | 0 | 100 | 0 | 100 | 0 |
| Morningglory | 25 | 4 | 100 | 0 | 100 | 0 | 100 | 0 |
| Nutsedge | 0 | 5 | 0 | 5 | 0 | 5 | 50 | 4 |

*Entries under K refer to percent kill; under V, to plant vigor, a vigor of 5 signifying no chemical injury.

TABLE 38
EFFECT OF APPLICATION LEVEL ON POSTEMERGENCE PERFORMANCE OF 6-CYCLOPROPYLAMINO-2-ISOPROPYLAMINO-4-METHOXY-5-PYRIMIDINECARBONITRILE
(Example LIV)*

| Crop | 0.14 kg/ha K | V | 0.28 kg/ha K | V | 0.56 kg/ha K | V | 1.12 kg/ha K | V | 2.24 kg/ha K | V |
|---|---|---|---|---|---|---|---|---|---|---|
| Lima Bean | 0 | 4 | 50 | 3 | 50 | 3 | 100 | 0 | 100 | 0 |
| Corn | 0 | 5 | 0 | 5 | 0 | 5 | 0 | 4 | 0 | 4 |
| Wild Oat | 0 | 5 | 0 | 4 | 100 | 0 | 100 | 0 | 100 | 0 |
| Lettuce | 100 | 0 | 100 | 0 | 100 | 0 | 100 | 0 | 100 | 0 |
| Mustard | 75 | 2 | 80 | 2 | 100 | 0 | 100 | 0 | 100 | 0 |
| Crabgrass | 50 | 4 | 50 | 4 | 100 | 0 | 100 | 0 | 100 | 0 |
| Tomato | 100 | 0 | 100 | 0 | 100 | 0 | 100 | 0 | 100 | 0 |
| Safflower | 100 | 0 | 100 | 0 | 100 | 0 | 100 | 0 | 100 | 0 |
| Flax | 100 | 0 | 100 | 0 | 100 | 0 | 100 | 0 | 100 | 0 |
| Wheat | 10 | 4 | 20 | 4 | 50 | 4 | 100 | 0 | 100 | 0 |
| Peanut | 0 | 5 | 0 | 5 | 0 | 5 | 0 | 5 | 0 | 5 |
| Soybean | 0 | 4 | 25 | 4 | 25 | 4 | 100 | 0 | 100 | 0 |
| Cotton | 0 | 5 | 0 | 5 | 0 | 4 | 50 | 4 | 90 | 2 |
| Rice | 0 | 5 | 0 | 4 | 25 | 4 | 100 | 0 | 100 | 0 |
| Sorghum | 0 | 5 | 0 | 5 | 0 | 4 | 100 | 0 | 100 | 0 |
| Barnyardgrass | 0 | 4 | 50 | 3 | 100 | 0 | 100 | 0 | 100 | 0 |
| Sicklepod | 0 | 4 | 75 | 3 | 100 | 0 | 100 | 0 | 100 | 0 |
| Morningglory | 0 | 4 | 0 | 4 | 100 | 0 | 100 | 0 | 100 | 0 |
| Nutsedge | 0 | 5 | 0 | 5 | 0 | 5 | 0 | 5 | 0 | 5 |

*Entries under K refer to percent kill; under V, to plant vigor, a vigor of 5 signifying no chemical injury.

TABLE 39
EFFECT OF APPLICATION LEVEL ON POSTEMERGENCE PERFORMANCE OF 6-CYCLOPROPYLAMINO-2-DIETHYAMINO-4-METHOXY-5-PYRIMIDINECARBONITRILE
(Example LV)*

| Crop | 0.56 kg/ha K | V | 1.12 kg/ha K | V | 2.24 kg/ha K | V | 4.48 kg/ha K | V | 8.96 kg/ha K | V |
|---|---|---|---|---|---|---|---|---|---|---|
| Lima Bean | 0 | 5 | 0 | 5 | 0 | 5 | 0 | 4 | 0 | 3 |
| Corn | 0 | 5 | 0 | 5 | 0 | 5 | 0 | 5 | 0 | 5 |
| Wild Oats | 100 | 0 | 100 | 0 | 100 | 0 | 100 | 0 | 100 | 0 |
| Lettuce | 100 | 0 | 100 | 0 | 100 | 0 | 100 | 0 | 100 | 0 |
| Mustard | 75 | 4 | 100 | 0 | 100 | 0 | 100 | 0 | 100 | 0 |
| Crabgrass | 25 | 4 | 50 | 4 | 100 | 0 | 100 | 0 | 100 | 0 |
| Nutsedge | 0 | 5 | 0 | 5 | 0 | 5 | 0 | 5 | 0 | 5 |

*Entries under K refer to percent kill; under V to plant vigor, a vigor of 5 signifying no chemical injury.

TABLE 40
EFFECT OF APPLICATION LEVEL ON POSTEMERGENCE PERFORMANCE OF 2-CYCLOPROPYLAMINO-6-ISOPROPYLAMINO-4-METHOXY-5-PYRIMIDINECARBONITRILE
(Example LVIII)*

| Crop | 0.56 kg/ha K | V | 1.12 kg/ha K | V | 2.24 kg/ha K | V | 4.48 kg/ha K | V | 8.96 kg/ha K | V |
|---|---|---|---|---|---|---|---|---|---|---|
| Lima Bean | 0 | 4 | 0 | 4 | 0 | 4 | 0 | 4 | 0 | 4 |
| Corn | 0 | 5 | 0 | 5 | 0 | 5 | 0 | 5 | 0 | 5 |
| Wild Oats | 0 | 5 | 0 | 5 | 0 | 5 | 0 | 5 | 20 | 4 |
| Lettuce | 100 | 0 | 100 | 0 | 100 | 0 | 100 | 0 | 100 | 0 |
| Mustard | 75 | 2 | 75 | 2 | 75 | 2 | 90 | 1 | 100 | 0 |
| Crabgrass | 0 | 5 | 0 | 4 | 0 | 3 | 0 | 3 | 0 | 3 |
| Nutsedge | 0 | 5 | 0 | 5 | 0 | 5 | 0 | 5 | 0 | 5 |

*Entries under K refer to percent kill; under V to plant vigor, a vigor of 5 signifying no chemical injury.

TABLE 41
EFFECT OF APPLICATION LEVEL ON POSTEMERGENCE PERFORMANCE OF 2,6-BIS(CYCLOPROPYLAMINO)-4-METHOXY-5-PYRIMIDINECARBONITRILE
(Example LIX)*

| Crop | 0.56 kg/ha K | V | 1.12 kg/ha K | V | 2.24 kg/ha K | V |
|---|---|---|---|---|---|---|
| Lima Bean | 100 | 0 | 100 | 0 | 100 | 0 |
| Corn | 0 | 5 | 0 | 5 | 0 | 4 |
| Wild Oats | 0 | 4 | 50 | 3 | 100 | 0 |
| Lettuce | 100 | 0 | 100 | 0 | 100 | 0 |
| Mustard | 75 | 3 | 100 | 0 | 100 | 0 |
| Crabgrass | 0 | 4 | 100 | 0 | 100 | 0 |
| Nutsedge | 0 | 5 | 0 | 5 | 0 | 5 |

*Entries under K refer to percent kill; under V to plant vigor, a vigor of 5 signifying no chemical injury.

TABLE 42
EFFECT OF APPLICATION LEVEL ON POSTEMERGENCE PERFORMANCE OF 6-CYCLOPROPYLAMINO-4-METHOXY-2-(1-METHYLPROPYLAMINO)-5-PYRIMIDINECARBONITRILE
(Example LX)*

| Crop | 0.14 kg/ha K | V | 0.28 kg/ha K | V | 0.56 kg/ha K | V | 1.12 kg/ha K | V | 2.24 kg/ha K | V |
|---|---|---|---|---|---|---|---|---|---|---|
| Lima Bean | 60 | 3 | 60 | 3 | 80 | 2 | 80 | 2 | 100 | 0 |
| Corn | 0 | 5 | 0 | 5 | 0 | 5 | 0 | 4 | 0 | 4 |
| Wild Oats | 0 | 4 | 20 | 3 | 80 | 2 | 70 | 2 | 90 | 2 |
| Lettuce | 100 | 0 | 100 | 0 | 100 | 0 | 100 | 0 | 100 | 0 |
| Mustard | 60 | 3 | 80 | 3 | 100 | 0 | 100 | 0 | 100 | 0 |
| Crabgrass | 20 | 4 | 60 | 4 | 60 | 2 | 70 | 2 | 100 | 0 |
| Soybean | 0 | 4 | 50 | 3 | 30 | 3 | 80 | 3 | 80 | 3 |
| Sorghum | 0 | 3 | 0 | 3 | 20 | 3 | 20 | 3 | 70 | 3 |
| Sesbania | 100 | 0 | 100 | 0 | 100 | 0 | 100 | 0 | 100 | 0 |
| Sicklepod | 60 | 3 | 100 | 0 | 100 | 0 | 100 | 0 | 100 | 0 |
| Green Foxtail | 100 | 0 | 70 | 3 | 100 | 0 | 100 | 0 | 100 | 0 |
| Peanuts | 0 | 4 | 0 | 4 | 0 | 3 | 0 | 3 | 100 | 0 |
| Cotton | 70 | 3 | 80 | 3 | 80 | 3 | 100 | 0 | 100 | 0 |
| Barnyardgrass | 0 | 3 | 60 | 3 | 60 | 3 | 100 | 0 | 100 | 0 |

TABLE 42-continued
EFFECT OF APPLICATION LEVEL ON POSTEMERGENCE PERFORMANCE OF 6-CYCLOPROPYLAMINO-4-METHOXY-2-(1-METHYLPROPYLAMINO)-5-PYRIMIDINECARBONITRILE
(Example LX)*

| Crop | 0.14 kg/ha | | 0.28 kg/ha | | 0.56 kg/ha | | 1.12 kg/ha | | 2.24 kg/ha | |
|---|---|---|---|---|---|---|---|---|---|---|
| | K | V | K | V | K | V | K | V | K | V |
| Johnsongrass | 40 | 4 | 50 | 4 | 70 | 3 | 70 | 3 | 95 | 2 |
| Downeybrome | 0 | 4 | 95 | 3 | 90 | 3 | 100 | 0 | 100 | 0 |
| Morningglorry | 0 | 4 | 0 | 4 | 0 | 3 | 100 | 0 | 100 | 0 |

*Entries under K refer to percent kill; under V to plant vigor, a vigor of 5 signifying no chemical injury.

TABLE 43
EFFECT OF APPLICATION LEVEL ON POSTEMERGENCE PERFORMANCE OF 4-METHOXY-6-(1-METHYLETHYLAMINO)-2-(2-METHYLPROPYLAMINO)-5-PYRIMIDINECARBONITRILE
(Example LXI)*

| Crop | 0.14 kg/ha | | 0.28 kg/ha | | 0.56 kg/ha | |
|---|---|---|---|---|---|---|
| | K | V | K | V | K | V |
| Lima Bean | 0 | 4 | 0 | 3 | 0 | 3 |
| Corn | 0 | 5 | 0 | 5 | 0 | 5 |
| Wild Oats | 0 | 4 | 0 | 4 | 20 | 3 |
| Lettuce | 0 | 4 | 20 | 4 | 100 | 0 |
| Mustard | 0 | 4 | 0 | 4 | 30 | 3 |
| Crabgrass | 20 | 3 | 30 | 3 | 70 | 3 |
| Soybean | 0 | 5 | 0 | 4 | 0 | 3 |
| Sorghum | 0 | 5 | 0 | 5 | 0 | 4 |
| Sesbania | 95 | 2 | 100 | 0 | 100 | 0 |
| Sicklepod | 0 | 4 | 30 | 3 | 30 | 3 |
| Green Foxtail | 95 | 3 | 95 | 2 | 90 | 3 |
| Peanuts | 0 | 4 | 0 | 4 | 0 | 4 |
| Cotton | 0 | 5 | 0 | 4 | 0 | 5 |
| Barnyardgrass | 0 | 5 | 0 | 4 | 0 | 3 |
| Johnsongrass | 0 | 5 | 0 | 4 | 20 | 4 |
| Downeybrome | 0 | 4 | 0 | 4 | 30 | 3 |
| Morningglorry | 0 | 5 | 0 | 5 | 0 | 5 |

*Entries under K refer to percent kill; under V to plant vigor, a vigor of 5 signifying no chemical injury.

The following herbicidal 5-pyrimidinecarbonitriles are prepared by the methods described above. In general, although these compounds exhibit herbicidal activity, a number of them are not as effective as the preferred active compounds: 6-amino-2-ethylamino-4-methoxy-5-pyrimidinecarbonitrile, 2-(1-cyano-1-methylethylamino)-4-methoxy-6-propylamino-5-pyrimidinecarbonitrile, 6-cyclopropylamino-2-isopropylamino-4-methoxy-5-pyrimidinecarbonitrile, 2-diethylamino-4-methoxy-6-methylamino-5-pyrimidinecarbonitrile, 2-diethylamino-6-dimethylamino-4-methoxy-5-pyrimidinecarbonitrile, 2-ethylamino-4-methoxy-6-propylamino-5-pyrimidinecarbonitrile, 2-diethylamino-4-methoxy-6-propylamino-5-pyrimidinecarbonitrile, 2-ethylamino-4-methoxy-6-methylamino-5-pyrimidinecarbonitrile, 6-dimethylamino-2-ethylamino-4-methoxy-5-pyrimidinecarbonitrile, 6-isopropylamino-4-methoxy-2-(1-methylpropylamino)-5-pyrimidinecarbonitrile, 2-isopropylamino-4-methoxy-6-(1-methylpropylamino)-5-pyrimidinecarbonitrile, 2-isopropylamino-4-methoxy-6-propylamino-5-pyrimidinecarbonitrile, 2-isopropylamino-4-methoxy-6-(2-methylpropylamino)-5-pyrimidinecarbonitrile, 6-ethylamino-4-methoxy-2-methylethylamino-5-pyrimidinecarbonitrile, 4-ethoxy-6-ethylamino-2-(1-cyano-1-methylethylamino)-5-pyrimidinecarbonitrile, 6-ethylamino-4-methoxy-2-(2-methylpropylamino)-5-pyrimidinecarbonitrile, 2-(1-cyano-1-methylpropylamino)-4-ethoxy-6-isopropylamino-5-pyrimidinecarbonitrile, 2,6-diethylamino-4-isopropoxy-5-pyrimidinecarbonitrile, 6-ethylamino-4-methoxy-2-(1-methylpropylamino)-5-pyrimidinecarbonitrile, 2-amino-6-ethylamino-4-methoxy-5-pyrimidinecarbonitrile, 2-amino-6-cyclopropylamino-4-methoxy-5-pyrimidinecarbonitrile, and 2-amino-6-isopropylamino-4-methoxy-5-pyrimidinecarbonitrile.

The active 5-pyrimidinecarbonitriles of this invention may be utilized in diverse formulations to produce the herbicidal compositions contemplated herein. The herbicidal compositions contain between about 0.5% and 95% active 5-pyrimidinecarbonitrile, together with between about 4% and 98.5% agriculturally acceptable carrier, and between about 1% and 15% surfactant, by weight. As is well known in the art, the formulation and mode of application of an herbicidal composition may affect its activity in a given application. Thus, the herbicidal 5-pyrimidinecarbonitriles disclosed herein may be formulated into granules, wettable powders, emulsifiable concentrates, solutions, or other known forms, depending on the mode of application.

Granular formulations are particularly useful for aerial application. These formulations may be of several types. Large particles of an absorbent carrier such as attapulgite or kaolin clay, corncobs, expanded mica, and so forth, may be impregnated with solutions of the active compounds. The active 5-pyrimidinecarbonitriles in solution or as a slurry may also be sprayed onto the surface of the absorbent particles. The core of the particle may be watersoluble or insoluble. A particularly useful type of particle is one in which a wettable powder is applied as a surface coating to an insoluble granule such that the wettable powder may be dispersed on contact with moisture. Granules may be produced by compacting dusts or powders, by extrusion through a die, or by use of a granulating disk. Granular formulations may vary widely in concentration, containing as little as 0.5% or as much as about 20% active compound.

Wettable powders in the form of finely divided particles, which disperse readily in water or other dispersants, are useful formulations for both preemergence and postemergence herbicides. A wettable powder typically contains a carrier such as a readily wetted inorganic diluent; for example, Fuller's earth, kaolin clays or silicas mixed with about 5% to 80%, but preferably at least 50%, herbicidally active compound and lesser amounts of surfactants.

Emulsifiable concentrates, which are homogeneous liquid or paste compositions dispersible in water or other dispersants, may consist entirely of the active 5-pyrimidinecarbonitriles of this invention together with a liquid or solid surfactant. They may also contain agriculturally acceptable liquid carriers such as xylene, naptha, isophorone or other organic solvents.

Typical surfactants used in agricultural formulations include, for example, the alkyl and aralkyl sulfonates and sulfates and their sodium salts, polyethylene oxides, sulfonated oils, fatty acid esters of polyhydric alcohols, and other types of surface active agents, many of which are available in commerce. Surfactants, when used, normally comprise from about 1% to 15% by weight of the herbicidal composition.

The herbicidal compositions of this invention may be applied without further dilution or as dilute solutions, emulsions, or suspensions in water or other suitable diluents. The herbicidal compositions may be applied to the area wherein control is desired by spraying the compositions onto the undesired vegetation or the surface of the soil if they are liquids, or by distribution from mechanical equipment in the case of solids. The surface-applied material may also be blended into the upper layer of soil by cultivation, or left as applied in order to gain the optimum results.

The herbically active compounds of this invention may be formulated and applied together with insecticides, fungicides, nematicides, fertilizers and other agricultural chemicals. In formulating and applying the herbicidal compositions of this invention, either alone or with other agricultural chemicals, herbicidally effective amounts of the active compounds are employed. The amount constituting an effective amount is variable, but generally, a uniform application of between about 0.1 and 9 kilograms per hectare is effective, for example, 0.28 to 4.48 kilograms per hectare.

It will be apparent to those skilled in the art that various modifications may be made in the formulation of the herbicidal compositions of this invention, and in their application, without departing from the scope and spirit of this invention as defined in the following claims:

I claim:

1. A chemical compound having the structural formula

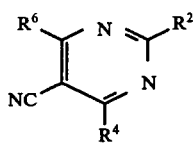

wherein
(a) $R^2$ is a radical selected from amino, lower alkylamino, lower cycloalkylamino, di(lower alkyl)amino, amino, and halogen;
(b) $R^4$ is a radical selected from lower alkoxy and halogen; and
(c) $R^6$ is a radical selected from amino, lower alkylamino, lower cycloalkylamino, di(lower alkyl)amino, and halogen;

with the proviso that no more than two of $R^2$, $R^4$, and $R^6$ are halogen; and provided further that neither $R^2$ nor $R^6$ is tert-butylamino; and when $R^2$ is isopropylamino, $R^6$ is other than n-butylamino; and when $R^2$ is methylethylamino, $R^6$ is other than isopropylamino; and when $R^2$ is diethylamino, $R^6$ is other than amino.

2. A chemical compound of claim 1 wherein the halogen is chlorine.

3. A chemical compound having the structural formula

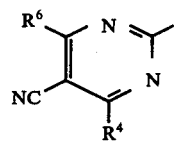

wherein
(a) $R^2$ is a radical selected from amino, lower alkylamino, lower cycloalkylamino, di(lower alkyl)amino, and amino;
(b) $R^4$ is a lower alkoxy radical; and
(c) $R^6$ is a radical selected from amino, lower alkylamino, lower cycloalkylamino, and di(lower alkyl)amino;

with the proviso that neither $R^2$ nor $R^6$ is tert-butylamino; and provided further that when $R^2$ is isopropylamino, $R^6$ is other than n-butylamino; and when $R^2$ is methylethylamino, $R^6$ is other than isopropylamino; and when $R^2$ is diethylamino, $R^6$ is other than amino.

4. A chemical compound of claim 3 wherein $R^2$ is selected from lower alkylamino (except tert-butylamino) and amino; and $R^6$ is selected from lower alkylamino (except tert-butylamino) and lower cycloalkylamino.

5. A chemical compound of claim 4 wherein $R^2$ is selected from ethylamino, isopropylamino, 1-methylpropylamino, 2-methylpropylamino, and 1-cyano-1-methylethylamino; $R^4$ is methoxy or ethoxy; and $R^6$ is selected from ethylamino, isopropylamino and cyclopropylamino.

6. The chemical compound of claim 5 which is 2-(1-cyano-1-methylethylamino)-6-ethylamino-4-methoxy-5-pyrimidinecarbonitrile.

7. The chemical compound of claim 5 which is 2-(1-cyano-1-methylethylamino)-6-cyclopropyl-amino-4-methoxy-5-pyrimidinecarbonitrile.

8. The chemical compound of claim 5 which is 2-(1-cyano-1-methylethylamino)-6-isopropylamino-4-methoxy-5-pyrimidinecarbonitrile.

9. An herbicidal composition comprising an herbicidally effective amount of at least one of the chemical compounds of claim 3 in admixture with an agriculturally acceptable carrier and a surfactant.

10. An herbicidal composition of claim 9 wherein $R^2$ is selected from lower alkylamino (except tert-butylamino) and amino; and $R^6$ is selected from lower alkylamino (except tert-butylamino) and lower cycloalkylamino.

11. An herbicidal composition of claim 10 wherein $R^2$ is selected from ethylamino, isopropylamino, 1-methylpropylamino, 2-methylpropylamino, and 1-cyano-1-methylethylamino; $R^4$ is methoxy or ethoxy; and $R^6$ is selected from ethylamino, isopropylamino and cyclopropylamino.

12. An herbicidal composition of claim 11 in which the chemical compound is 2-(1-cyano-1-methylethylamino)-6-ethylamino-4-methoxy-5-pyrimidinecarbonitrile.

13. An herbicidal composition of claim 11 in which the chemical compound is 2-(1-cyano-1-methylethylamino)-6-cyclopropylamino-4-methoxy-5-pyrimidinecarbonitrile.

14. An herbicidal composition of claim 11 in which the chemical compound is 2-(1-cyano-1-methylethylamino)-6-isopropylamino-4-methoxy-5-pyrimidinecarbonitrile.

15. A method of controlling plant growth which comprises applying to the locus of the plants an herbicidally effective amount of a chemical compound of claim 3.

16. A method of claim 15 wherein the chemical compound is selected from 2-(1-cyano-1-methylethylamino)-6-isopropylamino-4-methoxy-5-pyrimidinecarbonitrile, 2-(1-cyano-1-methylethylamino)-6-ethylamino-4-methoxy-5-pyrimidinecarbonitrile, and 2-(1-cyano-1-methylethylamino)-6-cyclopropylamino-4-methoxy-5-pyrimidinecarbonitrile.

17. A method of claim 16 wherein the growth of weeds is controlled without substantially affecting Zea mays in the same locus.

18. A method of claim 16 wherein the growth of weeds is controlled without substantially affecting Gossypium hirsutum in the same locus.

19. The method of claim 18 wherein the chemical compound is 2-(1-cyano-1-methylethylamino)-6-isopropylamino-4-methoxy-5-pyrimidinecarbonitrile.

20. A method of claim 16 wherein the growth of weeds is controlled without substantially affecting Sorghum vulgare in the same locus.

21. A method of claim 16 wherein the growth of weeds is controlled without substantially affecting Glycine max in the same locus.

22. A method of claim 16 wherein the growth of weeds is controlled without substantially affecting *Arachis hypogaea* in the same locus.

* * * * *

UNITED STATES PATENT AND TRADEMARK OFFICE
CERTIFICATE OF CORRECTION

PATENT NO. : 4,092,150
DATED : May 30, 1978
INVENTOR(S) : Gino R. Treves

It is certified that error appears in the above-identified patent and that said Letters Patent are hereby corrected as shown below:

Col. 1, line 10, change "This is a continuation-in-part of application Ser." to read --This invention pertains to the general field of herbi- --.

Col. 43, line 51, change ")amino, amino, and halogen;" to read --)amino, [alpha-cyano(lower alkyl)]amino, and halogen;--.

Col. 44, line 12, change ")amino, and amino;" to read --)amino, and [alpha-cyano(lower alkyl)]amino;--;

Col. 44, line 25, change "and amino;" to read --and [alpha-cyano-(lower alkyl)]amino;--;

Col. 44, line 49, change "and amino;" to read --and [alpha-cyano(lower alkyl)]amino;--.

Signed and Sealed this

Thirteenth Day of February 1979

[SEAL]

Attest:

RUTH C. MASON
Attesting Officer

DONALD W. BANNER
Commissioner of Patents and Trademarks